(12) United States Patent
Dreher et al.

(10) Patent No.: US 10,231,915 B2
(45) Date of Patent: *Mar. 19, 2019

(54) COMPOSITIONS FOR ALTERING THE COLOR OF HAIR

(71) Applicant: L'OREAL, Paris (FR)

(72) Inventors: Kimberly Dreher, Old Bridge, NJ (US); Gérard Provot, Saint-Ouen (FR); Dariusz Danielski, Chicago, IL (US); Fabien Boulineau, Livingston, NJ (US); Caroline Rahmouna Francoise Goget, Summit, NJ (US); Anthony Potin, Hoboken, NJ (US); Allison Chin, Hoboken, NJ (US); Michael DeGeorge, Old Bridge, NJ (US); Mara Applebaum, Plainfield, NJ (US); Mary Abraam Soliman, Kendall Park, NJ (US); Ashley Ann Figatner, Lawrenceville, NJ (US); Megan Pauker, South Plainfield, NJ (US); Emmanuel Appiah-Amponsah, Metuchen, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/484,625

(22) Filed: Apr. 11, 2017

(65) Prior Publication Data

US 2018/0042830 A1  Feb. 15, 2018

Related U.S. Application Data

(63) Continuation-in-part of application No. PCT/US2016/030172, filed on Apr. 29, 2016.

(60) Provisional application No. 62/155,900, filed on May 1, 2015, provisional application No. 62/155,931, filed on May 1, 2015.

(51) Int. Cl.
| | |
|---|---|
| *A61K 8/41* | (2006.01) |
| *A61Q 5/00* | (2006.01) |
| *A61Q 5/04* | (2006.01) |
| *A61Q 5/12* | (2006.01) |
| *A61K 8/24* | (2006.01) |
| *A61K 8/365* | (2006.01) |
| *A61K 8/44* | (2006.01) |
| *A61Q 5/06* | (2006.01) |
| *A61Q 5/10* | (2006.01) |
| *A61K 8/86* | (2006.01) |
| *A61K 8/362* | (2006.01) |

(52) U.S. Cl.
CPC .............. *A61K 8/41* (2013.01); *A61K 8/24* (2013.01); *A61K 8/362* (2013.01); *A61K 8/365* (2013.01); *A61K 8/44* (2013.01); *A61K 8/86* (2013.01); *A61Q 5/00* (2013.01); *A61Q 5/04* (2013.01); *A61Q 5/065* (2013.01); *A61Q 5/10* (2013.01); *A61Q 5/12* (2013.01); *A61K 2800/43* (2013.01); *A61K 2800/88* (2013.01)

(58) Field of Classification Search
CPC ...... A61K 2800/4324; A61K 2800/882; A61Q 5/08; A61Q 5/10
See application file for complete search history.

(56) References Cited

U.S. PATENT DOCUMENTS

| | | | |
|---|---|---|---|
| 2,261,002 | A | 10/1941 | Ritter |
| 2,271,378 | A | 1/1942 | Searle |
| 2,273,780 | A | 2/1942 | Dittmar |
| 2,375,853 | A | 5/1945 | Kirby et al. |
| 2,388,614 | A | 11/1945 | Kirby et al. |
| 2,454,547 | A | 11/1948 | Bock et al. |
| 2,850,351 | A | 9/1958 | Moore et al. |
| 2,961,347 | A | 11/1960 | Floyd |
| 3,142,623 | A | 7/1964 | Zviak et al. |
| 3,193,464 | A | 7/1965 | Edman et al. |
| 3,206,462 | A | 9/1965 | McCarty |
| 3,227,615 | A | 1/1966 | Korden |
| 3,472,243 | A | 10/1969 | Wall et al. |
| 3,472,840 | A | 10/1969 | Stone et al. |
| 3,589,978 | A | 6/1971 | Kamal et al. |
| 3,632,559 | A | 1/1972 | Matter et al. |
| 3,840,656 | A | 10/1974 | Kalopissis et al. |
| 3,874,870 | A | 4/1975 | Green et al. |
| 3,917,817 | A | 11/1975 | Vanlerberghe et al. |
| 3,929,990 | A | 12/1975 | Green et al. |
| 3,966,904 | A | 6/1976 | Green et al. |

(Continued)

FOREIGN PATENT DOCUMENTS

| | | |
|---|---|---|
| CN | 102451117 A | 5/2012 |
| CN | 105267066 A | 1/2016 |

(Continued)

OTHER PUBLICATIONS

International Preliminary Report on Patentability for PCT/US2016/30172, dated Jun. 19, 2017.

(Continued)

*Primary Examiner* — Andrew S Rosenthal

(74) *Attorney, Agent, or Firm* — The Marbury Law Group, PLLC

(57) ABSTRACT

The disclosure relates to systems and compositions comprising the systems for use in chemical treatment of keratinous substrates, such as the hair. The systems and compositions comprising the systems comprise at least one active agent and at least one acid. Methods of treating keratinous substrates with the systems and compositions comprising the systems are also disclosed.

7 Claims, 2 Drawing Sheets

(56) References Cited

U.S. PATENT DOCUMENTS

| | | |
|---|---|---|
| 4,001,432 A | 1/1977 | Green et al. |
| 4,003,699 A | 1/1977 | Rose et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,166,894 A | 9/1979 | Schaper |
| 4,172,887 A | 10/1979 | Vanlerberghe et al. |
| RE30,199 E | 1/1980 | Rose et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,412,943 A | 11/1983 | Hirota et al. |
| 4,422,853 A | 12/1983 | Jacquet et al. |
| 4,425,132 A | 1/1984 | Grollier et al. |
| 4,532,950 A | 8/1985 | Lang et al. |
| 4,579,732 A | 4/1986 | Grollier et al. |
| 4,591,610 A | 5/1986 | Grollier |
| 4,608,250 A | 8/1986 | Jacquet et al. |
| 4,761,273 A | 8/1988 | Grollier et al. |
| 4,770,873 A | 9/1988 | Wolfram et al. |
| 4,777,040 A | 10/1988 | Grollier et al. |
| 4,793,993 A | 12/1988 | Siuta-Mangano et al. |
| 4,812,307 A | 3/1989 | Siuta-Mangano |
| 4,834,971 A | 5/1989 | Klenk et al. |
| 4,948,579 A | 8/1990 | Jacquet et al. |
| 4,970,066 A | 11/1990 | Grollier et al. |
| 5,061,289 A | 10/1991 | Clausen et al. |
| 5,143,518 A | 9/1992 | Madrange et al. |
| 5,196,189 A | 3/1993 | Jacquet et al. |
| 5,221,286 A | 6/1993 | Singleton et al. |
| 5,350,572 A | 9/1994 | Savaides et al. |
| 5,356,438 A | 10/1994 | Kim et al. |
| 5,380,340 A | 1/1995 | Neunhoeffer et al. |
| 5,534,267 A | 7/1996 | Neunhoeffer et al. |
| 5,565,216 A | 10/1996 | Cowsar et al. |
| 5,628,991 A | 5/1997 | Samain et al. |
| 5,651,960 A | 7/1997 | Chan et al. |
| 5,656,265 A | 8/1997 | Bailey et al. |
| 5,663,366 A | 9/1997 | Neunhoeffer et al. |
| 5,688,291 A | 11/1997 | Said et al. |
| 5,708,151 A | 1/1998 | Mockli |
| 5,766,576 A | 6/1998 | Lowe et al. |
| 5,811,085 A | 9/1998 | Halloran |
| 5,833,966 A | 11/1998 | Samain |
| 6,099,592 A | 8/2000 | Vidal et al. |
| 6,173,717 B1 | 1/2001 | Schonert et al. |
| 6,284,003 B1 | 9/2001 | Rose et al. |
| 6,309,426 B1 | 10/2001 | Dias et al. |
| 6,338,741 B1 | 1/2002 | Vidal et al. |
| 6,348,189 B1 | 2/2002 | Tanabe et al. |
| 6,348,200 B1 | 2/2002 | Nakajima et al. |
| 6,398,821 B1 | 6/2002 | Dias et al. |
| 6,458,906 B1 | 10/2002 | Torgerson et al. |
| 6,515,050 B1 | 2/2003 | Mitsuzuka et al. |
| 6,537,532 B1 | 3/2003 | Torgerson et al. |
| 6,569,412 B2 | 5/2003 | Yamaguchi et al. |
| 6,645,258 B2 | 11/2003 | Vidal et al. |
| 6,706,258 B1 | 3/2004 | Gallagher et al. |
| 6,730,789 B1 | 5/2004 | Birault et al. |
| 6,984,250 B1 | 1/2006 | Legrand et al. |
| 7,041,142 B2 | 5/2006 | Chan et al. |
| 7,044,986 B2 | 5/2006 | Ogawa et al. |
| 7,390,479 B2 | 6/2008 | Sockel et al. |
| 7,598,213 B2 | 10/2009 | Geary et al. |
| 7,815,901 B2 | 10/2010 | Mathonneau et al. |
| 7,972,388 B2 | 7/2011 | Hamilton et al. |
| 8,298,519 B2 | 10/2012 | Adams et al. |
| 8,388,701 B2 * | 3/2013 | Uellner ............... A61K 8/04 |
| | | 8/405 |
| 8,613,913 B2 | 12/2013 | Chang et al. |
| 8,642,659 B2 | 2/2014 | Springer et al. |
| 9,095,518 B2 | 8/2015 | Pressly et al. |
| 9,144,537 B1 | 9/2015 | Pressly et al. |
| 9,175,114 B2 | 11/2015 | Puerta et al. |
| 9,180,086 B2 | 11/2015 | Cabourg et al. |
| 9,326,926 B2 | 5/2016 | Pressly et al. |
| 9,498,419 B2 | 11/2016 | Pressly et al. |
| 9,610,241 B2 | 4/2017 | Cabourg et al. |
| 2001/0042276 A1 | 11/2001 | Kawasoe et al. |
| 2001/0052354 A1 | 12/2001 | Nishibe et al. |
| 2002/0029429 A1 | 3/2002 | Dias et al. |
| 2002/0032933 A1 | 3/2002 | Dias et al. |
| 2002/0050013 A1 | 5/2002 | Vidal et al. |
| 2002/0053110 A1 | 5/2002 | Dias et al. |
| 2002/0155081 A1 | 10/2002 | Coope |
| 2002/0189034 A1 * | 12/2002 | Kitabata ............... A61K 8/19 |
| | | 8/405 |
| 2003/0019051 A9 | 1/2003 | Vidal et al. |
| 2003/0049222 A1 | 3/2003 | Akhter et al. |
| 2003/0072962 A1 | 4/2003 | Matsuzaki et al. |
| 2003/0152543 A1 | 8/2003 | Legrand et al. |
| 2004/0034944 A1 | 2/2004 | Legrand et al. |
| 2004/0034946 A1 | 2/2004 | Legrand et al. |
| 2004/0067212 A1 | 4/2004 | Tokuyama et al. |
| 2004/0086475 A1 | 5/2004 | Boswell et al. |
| 2004/0088800 A1 | 5/2004 | Cotteret |
| 2004/0181883 A1 | 9/2004 | Legrand et al. |
| 2004/0216244 A1 | 11/2004 | Cotteret et al. |
| 2004/0228580 A1 | 11/2004 | Lee et al. |
| 2004/0258652 A1 | 12/2004 | Pascaly et al. |
| 2005/0036970 A1 | 2/2005 | Sabbagh et al. |
| 2005/0087718 A1 | 4/2005 | Okada |
| 2005/0201966 A1 | 9/2005 | Ueyama et al. |
| 2006/0024257 A1 | 2/2006 | Chang et al. |
| 2006/0166845 A1 | 7/2006 | Terada |
| 2006/0198807 A1 | 9/2006 | Morioka |
| 2006/0228316 A1 | 10/2006 | Cannell et al. |
| 2007/0041921 A1 | 2/2007 | Neill et al. |
| 2007/0067924 A1 | 3/2007 | Beck et al. |
| 2007/0116661 A1 | 5/2007 | Mata |
| 2007/0160560 A1 | 7/2007 | Laurent et al. |
| 2007/0261594 A1 | 11/2007 | Vaskelis et al. |
| 2007/0264208 A1 | 11/2007 | Mougin et al. |
| 2008/0066773 A1 | 3/2008 | Anderson et al. |
| 2008/0138309 A1 | 6/2008 | Malle et al. |
| 2008/0141468 A1 | 6/2008 | Cottert |
| 2008/0187506 A1 | 8/2008 | Carballada et al. |
| 2008/0233072 A1 | 9/2008 | Bureiko et al. |
| 2009/0022681 A1 | 1/2009 | Carballada et al. |
| 2009/0126756 A1 | 5/2009 | Syed et al. |
| 2009/0252697 A1 | 10/2009 | Barbarat et al. |
| 2010/0004391 A1 | 1/2010 | Haddleton et al. |
| 2010/0081716 A1 | 4/2010 | Matsunaga et al. |
| 2010/0154140 A1 | 6/2010 | Simonet et al. |
| 2010/0158964 A1 | 6/2010 | Cunningham et al. |
| 2010/0202998 A1 | 8/2010 | Ramos-Stanbury et al. |
| 2010/0303748 A1 | 12/2010 | Hercouet |
| 2011/0061671 A1 | 3/2011 | Neplaz et al. |
| 2011/0256084 A1 | 10/2011 | Dixon et al. |
| 2012/0015894 A1 | 1/2012 | Terada |
| 2012/0022037 A1 | 1/2012 | Terada |
| 2012/0064137 A1 | 3/2012 | Kawai |
| 2012/0180807 A1 | 7/2012 | Flohr |
| 2012/0244082 A1 | 9/2012 | Sulzback et al. |
| 2013/0034515 A1 | 2/2013 | Stone et al. |
| 2013/0102513 A1 | 4/2013 | Terada |
| 2013/0118996 A1 | 5/2013 | Kaplan |
| 2013/0149274 A1 | 6/2013 | Nguyen et al. |
| 2013/0152959 A1 | 6/2013 | Genain et al. |
| 2013/0172518 A1 | 7/2013 | Huang et al. |
| 2013/0309190 A1 | 11/2013 | Dimotakis et al. |
| 2014/0158150 A1 | 6/2014 | Schoepgens et al. |

(56) References Cited

U.S. PATENT DOCUMENTS

| | | | |
|---|---|---|---|
| 2014/0186283 | A1 | 7/2014 | Cabourg et al. |
| 2014/0196741 | A1 | 7/2014 | Cabourg et al. |
| 2015/0034117 | A1 | 2/2015 | Pressly et al. |
| 2015/0034119 | A1 | 2/2015 | Pressly et al. |
| 2015/0053228 | A1 | 2/2015 | Bonauer et al. |
| 2015/0053230 | A1 | 2/2015 | Myatt |
| 2015/0157544 | A1 | 6/2015 | Briggs et al. |
| 2015/0252302 | A1 | 9/2015 | Rieth et al. |
| 2015/0283041 | A1 | 10/2015 | Benn et al. |
| 2015/0297496 | A1 | 10/2015 | Kroon et al. |
| 2015/0313816 | A1 | 11/2015 | Daubresse |
| 2015/0328102 | A1 | 11/2015 | Pressly et al. |
| 2016/0081899 | A1 | 3/2016 | Pressly et al. |
| 2016/0193129 | A1 | 7/2016 | Pressly et al. |
| 2016/0263003 | A1 | 9/2016 | Pressly et al. |
| 2016/0310394 | A1 | 10/2016 | Pressly et al. |
| 2016/0348037 | A1 | 12/2016 | Findlay et al. |
| 2017/0007518 | A1 | 1/2017 | Everaert et al. |
| 2017/0112740 | A1 | 4/2017 | Schoepgens et al. |
| 2017/0112743 | A1 | 4/2017 | Schoepgens et al. |
| 2017/0113071 | A1 | 4/2017 | Schoepgens et al. |
| 2017/0119122 | A1 | 5/2017 | Rautenberg-Groth et al. |
| 2017/0128334 | A1 | 5/2017 | Schoepgens et al. |
| 2017/0128342 | A1 | 5/2017 | Schoepgens et al. |
| 2017/0143611 | A1 | 5/2017 | Hippe et al. |
| 2017/0151143 | A1 | 6/2017 | Scheunemann et al. |
| 2017/0151144 | A1 | 6/2017 | Scheunemann et al. |
| 2017/0151146 | A1 | 6/2017 | Scheunemann et al. |
| 2017/0151147 | A1 | 6/2017 | Scheunemann et al. |
| 2017/0151156 | A1 | 6/2017 | Scheunemann et al. |
| 2017/0165161 | A1 | 6/2017 | Manneck et al. |

FOREIGN PATENT DOCUMENTS

| | | | |
|---|---|---|---|
| CN | 105902403 A | 8/2016 | |
| CN | 105902404 A | 8/2016 | |
| CN | 106265109 A | 1/2017 | |
| DE | 1220969 B | 7/1966 | |
| DE | 2225541 A1 | 12/1973 | |
| DE | 2359399 A1 | 6/1975 | |
| DE | 3843892 A1 | 6/1990 | |
| DE | 4133957 A1 | 4/1993 | |
| DE | 4300320 A1 | 7/1994 | |
| DE | 19543988 A1 | 5/1997 | |
| DE | 29722990 U1 | 5/1999 | |
| DE | 10051773 A1 | 4/2002 | |
| DE | 10051774 A1 | 4/2002 | |
| DE | 20208254 U1 | 8/2002 | |
| DE | 102004052480 A1 | 5/2006 | |
| DE | 202015104742 U1 | 10/2015 | |
| DE | 102014213317 A1 | 1/2016 | |
| DE | 102015223828 A1 | 9/2016 | |
| EP | 0122324 A1 | 10/1984 | |
| EP | 0298684 A2 | 1/1989 | |
| EP | 0299764 A2 | 1/1989 | |
| EP | 0512879 A2 | 11/1992 | |
| EP | 0636358 A1 | 2/1995 | |
| EP | 0714954 A2 | 6/1996 | |
| EP | 0770375 A1 | 5/1997 | |
| EP | 0978272 A1 | 2/2000 | |
| EP | 1174112 A2 | 1/2002 | |
| EP | 1779896 A2 | 5/2007 | |
| EP | 1810657 A1 | 7/2007 | |
| EP | 2123250 A1 | 11/2009 | |
| EP | 2295029 A1 | 3/2011 | |
| EP | 2460511 A1 | 6/2012 | |
| EP | 2471504 A1 | 7/2012 | |
| EP | 2478892 A1 | 7/2012 | |
| FR | 1492597 A | 8/1967 | |
| FR | 1583363 A | 10/1969 | |
| FR | 2162025 A | 7/1973 | |
| FR | 2252840 A1 | 6/1975 | |
| FR | 2270846 A1 | 12/1975 | |
| FR | 2280361 A2 | 2/1976 | |
| FR | 2316271 A1 | 1/1977 | |
| FR | 2320330 A1 | 3/1977 | |
| FR | 2336434 A1 | 7/1977 | |
| FR | 2368508 A2 | 5/1978 | |
| FR | 2413907 A1 | 8/1979 | |
| FR | 2505348 A1 | 11/1982 | |
| FR | 2542997 A1 | 9/1984 | |
| FR | 2733749 A1 | 11/1996 | |
| FR | 2801308 A1 | 5/2001 | |
| FR | 2886136 A1 | 12/2006 | |
| FR | 2975899 A1 | 12/2012 | |
| FR | 2975900 A1 | 12/2012 | |
| GB | 713675 A | 8/1954 | |
| GB | 741307 A | 11/1955 | |
| GB | 773559 A | 4/1957 | |
| GB | 1026978 A | 4/1966 | |
| GB | 1125794 A | 8/1968 | |
| GB | 1153196 A | 5/1969 | |
| GB | 1260451 A | 1/1972 | |
| GB | 1546809 A | 5/1979 | |
| GB | 1584364 A | 2/1981 | |
| JP | 02-019576 A | 1/1990 | |
| JP | H02-138110 | 5/1990 | |
| JP | 05-163124 A | 6/1993 | |
| JP | D8-198732 A | 8/1996 | |
| JP | 2006-327994 A | 12/2006 | |
| JP | 2009-007283 A | 1/2009 | |
| JP | 2010-155823 A | 7/2010 | |
| JP | 2016003185 A | 1/2016 | |
| JP | 2017095451 A | 6/2017 | |
| KP | 10-2001-0039848 A | 1/2003 | |
| KR | 10-2001-0039848 A | 7/2001 | |
| KR | 2003-0003970 A | 1/2003 | |
| KR | 10-2004-0098688 A | 11/2004 | |
| KR | 10-2006-0059564 A | 6/2006 | |
| KR | 10-2016-0064420 A | 11/2014 | |
| WO | 33/00882 A1 | 1/1993 | |
| WO | 93/08787 A2 | 5/1993 | |
| WO | 94/08969 A1 | 4/1994 | |
| WO | 94/08970 A1 | 4/1994 | |
| WO | 95/01152 A1 | 1/1995 | |
| WO | 95/01772 A1 | 1/1995 | |
| WO | 95/15144 A1 | 6/1995 | |
| WO | 96/15765 A1 | 5/1996 | |
| WO | 97/24106 A1 | 7/1997 | |
| WO | 98/56333 A1 | 12/1998 | |
| WO | 39/66793 A1 | 12/1999 | |
| WO | 01/47486 A1 | 7/2001 | |
| WO | 02/32383 A2 | 4/2002 | |
| WO | 02/32386 A2 | 4/2002 | |
| WO | 2006/011771 A1 | 2/2006 | |
| WO | 2006/134051 A1 | 12/2006 | |
| WO | 2007/038733 A1 | 4/2007 | |
| WO | 2009/024936 A2 | 2/2009 | |
| WO | 2010/049434 A2 | 5/2010 | |
| WO | 2011/134785 A2 | 11/2011 | |
| WO | 2012/080321 A2 | 6/2012 | |
| WO | 2012/084532 A2 | 6/2012 | |
| WO | 2012/164064 A1 | 12/2012 | |
| WO | 2015118357 A1 | 8/2013 | |
| WO | 2013/136480 A1 | 9/2013 | |
| WO | 2014/016407 A1 | 1/2014 | |
| WO | 2014072490 A1 | 5/2014 | |
| WO | 2014/118212 A1 | 8/2014 | |
| WO | 2014/125452 A1 | 8/2014 | |
| WO | 2014/167508 A1 | 10/2014 | |
| WO | 2014/207097 A1 | 12/2014 | |
| WO | 2015/017768 A1 | 2/2015 | |
| WO | 2015/026994 A1 | 2/2015 | |
| WO | 2015/058942 A1 | 4/2015 | |
| WO | 2015/075064 A2 | 5/2015 | |
| WO | 2015069823 A1 | 5/2015 | |
| WO | 2015/175986 A2 | 11/2015 | |
| WO | 2016005114 A1 | 1/2016 | |
| WO | 2016005144 A1 | 1/2016 | |
| WO | 2016091492 A1 | 6/2016 | |
| WO | 2016120642 A1 | 8/2016 | |
| WO | 20160198203 A1 | 12/2016 | |
| WO | 2017041903 A1 | 3/2017 | |
| WO | 2017041905 A1 | 3/2017 | |

(56) References Cited

FOREIGN PATENT DOCUMENTS

| WO | 2017041906 A1 | 3/2017 |
|---|---|---|
| WO | 2017041907 A1 | 3/2017 |
| WO | 2017041908 A1 | 3/2017 |
| WO | 2017041909 A1 | 3/2017 |
| WO | 2017041910 A1 | 3/2017 |
| WO | 2017059646 A1 | 4/2017 |
| WO | 2017085117 A1 | 5/2017 |
| WO | 2017/091796 A1 | 6/2017 |
| WO | 2017/091797 A1 | 6/2017 |
| WO | 2017/091800 A1 | 6/2017 |
| WO | 2017102936 A1 | 6/2017 |

OTHER PUBLICATIONS

Petition for Post-Grant Review of U.S. Pat. No. 9,498,419 filed Jan. 31, 2017, with Exhibits.
Copending U.S. Appl. No. 15/484,663, filed Apr. 11, 2017.
Copending U.S. Appl. No. 15/339,035, filed Oct. 31, 2016.
International Search Report and Written Opinion for counterpart PCT Application No. PCT/US2016/03172, dated Sep. 19, 2016.
International Search Report and Written Opinion for counterpart PCT Application No. PCT/US2016/063724, dated Feb. 2, 2017.
International Search Report and Written Opinion for counterpart PCT Application No. PCT/US2016/063727, dated Feb. 8, 2017.
International Search Report and Written Opinion for counterpart PCT Application No. PCT/US2016/063732, dated Feb. 6, 2017.
International Search Report and Written Opinion for counterpart PCT Application No. PCT/US2016/063728, dated Feb. 1, 2017.
Mintel: "Abundant Volume Conditioner," Alterna Professional Haircare, Database Record No. 2177147, Sep. 2013.
Mintel: "Hair Colourant," Catzy Hair Colourant, Database Record ID 743114, Jul. 2007, 4 pages.
Mintel: "Combing Cream," Devintex Cosmeticos, Database Record No. 1595490, Jul. 2011.
Mintel: "Combing Cream," Devintex Cosmeticos, Database Record No. 1595658, Jul. 2011.
Mintel: "Conditioner," Devintex Cosmeticos, Database Record No. 1595545, Jul. 2011.
Mintel: "Conditioner," Laperie Haircare, Database Record No. 3645337, Feb. 2016.
Mintel: "Conditioner," Laperie Haircare, Database Record No. 3790215, Feb. 2016.
Mintel: "Conditioner," Liqwd, Database Record No. 1172691, Sep. 2009.
Mintel: "Conditioner," TIGI, Database Record No. 1442418, Nov. 2010.
Mintel: "Conditioner," TIGI International, Database Record No. 1445427, Nov. 2010.
Mintel: "Conditioner," TGI International, Database Record No. 3280151, Jul. 2015.
Mintel, "Masque for Beautiful Color," Oribe Hair Care, Database Record No. 1522953, Mar. 2011.
Mintel: "Moisturizing Conditioner," Frederic Fekkai, Datablase Record No. 1507159, Mar. 2011.
Mintel: "Post-Service Perfector," Redken, Database Record No. 4326453, Nov. 2016.
Mintel: "Step 3-Conditioner," L'OREAL, Database Record No. 4353779, Oct. 2016.
Mintel: "Step 3-Conditioner," L'OREAL, Database Record No. 4609117, Feb. 2017.
Non-Final Office Action for copending U.S. Appl. No. 15/484,663, dated Jun. 21, 2017.
Final Office Action for copending U.S. Appl. No. 15/484,663, dated Nov. 28, 2017.
Non-Final Office Action for copending U.S. Appl. No. 15/339,035, dated Jan. 10, 2018.
Third Party Submission for copending U.S. Appl. No. 15/484,663, filed Feb. 28, 2018 with attachments.
U.S. Appl. No. 61/994,709, filed May 16, 2014.
Estetica: the hairstyling professional magazine, (http://estetica.it/int/a/schwarzkopf-professional-launches-fibreplex), "Schwarzkopf Professional Launches Fibreplex®," published Sep. 23, 2015 reporting that Fibreplex was launched during Sep. 2015.
Fibreplex® No. 1 Material Safety Data Sheet.
Fibreplex® No. 1 Product Label.
International Search Report for counterpart Application PCT/US2017/058495, dated Jan. 5, 2018.
International Preliminary Report on Patentability for counterpart Application No. PCT/US2016/063727, dated Jun. 7, 2018.
International Preliminary Report on Patentability for counterpart Application No. PCT/US2016/063732, dated Jun. 7, 2018.
International Preliminary Report on Patentability for counterpart Application No. PCT/US2016/063728, dated Jun. 7, 2018.
International Preliminary Report on Patentability for counterpart Application No. PCT/US2016/063724, dated Jun. 7, 2018.
Bayraktar, V.N., "Organic Acids Concentration in Wine Stocks After *Saccharomyces cereviisilae* Fermentation," Biotechnologia Acta, vol. 6, No. 2, Jan. 1, 2013, pp. 97-106.
Supplementary European Search Report for counterpart Application EP16789846, dated Oct. 30, 2018.
Non-Final Office Action for copending U.S. Appl. No. 15/339,035, dated Oct. 5, 2018.

* cited by examiner

COMPOSITIONS FOR ALTERING THE COLOR OF HAIR

PRIORITY

The present application claims priority as a continuation-in-part of International Application No. PCT/US16/30172, filed Apr. 29, 2016, which claims priority to U.S. Provisional Application Nos. 62/155,900 and 62/155,931, both filed May 1, 2015.

TECHNICAL FIELD

The present disclosure relates to systems and compositions for use in chemical treatment of keratinous substrates, such as the hair and nails. The systems and compositions comprise at least one active agent and at least one acid.

BACKGROUND

It is known that consumers desire to use cosmetic and personal care compositions that enhance the appearance of keratinous substrates such as hair, e.g., by changing the color, style, and/or shape of the hair and/or by imparting various properties to hair, such as shine and conditioning. Many of the known compositions and processes for enhancing the appearance of the hair involve chemical treatment of the hair.

The process of changing the color of hair, for example, can involve depositing an artificial color onto the hair which provides a different shade or color to the hair and/or lifting the color of the hair, such as lightening the color of dark hair to lighter shades. The process of lifting the color of hair, also known as lightening, generally requires the use of compositions that comprise at least one oxidizing agent.

Lightening or lifting the color of the hair is typically evaluated by the variation in tone height before and after the application of a hair color-altering composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels range from 1 (black) to 10 (light blond), one unit corresponding to one tone; thus, the higher the number, the lighter the shade or the greater the degree of lift.

In general, hair lightening or color lifting compositions and hair dyeing compositions possess an alkalinity such that these compositions have a pH value of above 7, typically being at pH 9 and above, and may generally require the presence of an alkalizing agent such as ammonia or an ammonia gas generating compound and/or an amine or ammonium-based compound in amounts sufficient to make such compositions alkaline. The alkalizing agent causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While such hair dyeing, color lifting, relaxing, straightening, perming, and waving compositions can effectively alter the color of hair, these chemical treatments can damage the hair fibers and/or irritate the scalp and may be accompanied by an undesirable odor of ammonia. Thus, in order to reduce or avoid the drawbacks mentioned above, as well as to improve the cosmetic performance of the treatment compositions, the use of new and additional ingredients and novel combinations of ingredients are continuously sought.

However, the choice of ingredients or combinations of ingredients could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It would therefore be desirable to provide the consumer with compositions and methods that can treat the hair, e.g. lift the color of hair and/or deposit color onto hair in an efficient manner, while providing other cosmetic advantages such as shine, conditioning, fiber strength, and/or a healthy appearance to the hair, but avoiding or minimizing damage to the hair.

Further, both natural and sensitized or chemically treated hair can contain several kinds of negatively charged moieties, for example carboxylates (resulting of the hydrolysis of amino acids and thioester bonds) and/or sulfonates (resulting from the oxidation of disulfide bonds). These negatively charged moieties can degrade the cosmetic properties of the hair. Moreover, when hair is chemically treated or damaged, the disulfide bonds in hair (disulfide linkages between two cysteine units) can be reduced or broken, resulting in the formation of thiol groups and/or cysteic acid.

Thus, one objective of the disclosure is to provide novel compositions that can provide advantageous effects such as strengthening of the hair fiber, protecting hair fibers from damage or further damage, enhanced properties such as softness, shine, conditioning, healthy appearance, while at the same time, providing desired effects such as coloring, lightening, straightening, relaxing, and/or shaping.

SUMMARY

The present disclosure relates to systems and compositions comprising the systems for treating keratinous substrates, such as the hair and nails, as well as methods for treating keratinous substrates with the systems and compositions comprising the systems disclosed herein.

In various exemplary and non-limiting embodiments, the systems and compositions comprising the systems may be useful for chemically treating the hair. Exemplary and non-limiting embodiments of the disclosure relate to compositions comprising systems of at least one active agent and at least one acid, in order to bring cosmetic (e.g. soft hair feel) and strengthening properties to the hair fibers. In various embodiments, the at least one active agent comprises at least one diamine molecule. In various embodiments, the systems and/or compositions comprising the systems are free or substantially free of crosslinking agents, and/or the at least one acid does not comprise any carbon-carbon double bonds.

Exemplary methods comprise applying a system or composition comprising the system of at least one active agent and at least one acid to the hair before, during, or after application of an oxidation dyeing or lightening composition, in order to deposit color onto the hair fiber, and/or to lift or lighten the color of the hair, while providing other cosmetic advantages such as shine, conditioning, fiber strength, and/or a healthy appearance to the hair and avoiding or minimizing damage to the hair.

Exemplary methods comprise applying a composition comprising a system of at least one active agent and at least one acid to the hair before, during, or after application of a hair shaping composition such as a relaxing composition, a straightening composition, a perming composition or a waving composition, in order to alter the shape of the hair, while providing other cosmetic advantages such as shine, conditioning, fiber strength, and/or a healthy appearance to the hair and avoiding or minimizing damage to the hair.

In order to achieve these and other advantages, the disclosure relates to systems or compositions comprising a system of at least active agent of formula (I) and at least one acid. In various embodiments, the systems and/or compositions comprising the systems are free or substantially free of crosslinking agents, and/or the at least one acid may be free or substantially free of carbon-carbon double bonds. The disclosure is also drawn to hair coloring or hair lightening compositions, as well as hair shaping compositions such as hair relaxers, straighteners, perms and waves, comprising the above-described system and/or composition comprising the system.

In various embodiments, the disclosure relates to systems and compositions comprising a system of at least active agent of formula (II) and at least one acid. In various embodiments, the at least one acid may be free or substantially free of carbon-carbon double bonds. The cosmetic compositions may be free or substantially free of crosslinking agents. The disclosure is also drawn to hair coloring or hair lightening compositions, as well as hair shaping compositions such as hair relaxers, straighteners, perms and waves, comprising the above-described system and/or composition comprising the system.

In further embodiments, the disclosure relates to systems and compositions comprising a system of at least active agent of formula (III) and at least one acid. In various embodiments, the at least one acid may be free or substantially free of carbon-carbon double bonds. The cosmetic compositions may be free or substantially free of crosslinking agents. The disclosure is also drawn to hair coloring or hair lightening compositions, as well as hair shaping compositions such as hair relaxers, straighteners, perms and waves, comprising the above-described system and/or composition comprising the system.

In yet further embodiments, the disclosure relates to cosmetic compositions comprising a system of at least one active agent comprising at least one diamine and at least one acid. In various embodiments, the at least one acid may be free or substantially free of carbon-carbon double bonds. The cosmetic compositions may be free or substantially free of crosslinking agents. The disclosure is also drawn to hair coloring or hair lightening compositions, as well as hair shaping compositions such as hair relaxers, straighteners, perms and waves, comprising the above-described system and/or composition comprising the system.

According to various embodiments, compositions according to the disclosure may comprise a system or composition comprising the system comprising, optionally in a cosmetically acceptable solvent: at least one active agent; at least one acid free of carbon-carbon double bonds; and optionally at least one cationic polymer. The disclosure is also drawn to hair coloring or hair lightening compositions, as well as hair shaping compositions such as hair relaxers, straighteners, perms and waves, comprising the above-described system and/or composition comprising the system. The systems and/or compositions may be free or substantially free of crosslinking agents.

According to various embodiments, compositions according to the disclosure may comprise a system or composition comprising the system comprising: at least one active agent, at least one acid free of carbon-carbon double bonds, and optionally at least one cationic polymer; and a composition for coloring or lightening the hair comprising: an oxidizing composition, and optionally, at least one colorant. The systems and/or compositions may be free or substantially free of crosslinking agents.

Various embodiments of the disclosure are drawn to processes for chemically treating the hair, for example by lifting or lightening the color of the hair or by shaping or changing the shape of hair using relaxers, straighteners, perms and waves. In one embodiment, the process comprises applying onto hair fibers, a system or composition comprising the system comprising the above-described system and oxidizing compositions; and leaving the composition on the hair fibers for a period of time sufficient to color or lighten the fibers. In another embodiment, the process comprises applying onto the hair fibers, a system or composition comprising the system comprising the above-described system and hair shaping compositions; and leaving the composition on the fibers for a period of time sufficient to shape or alter the shape of the fibers as desired. Such processes may, in at least some embodiments, provide shine, conditioning, fiber strength, and/or a healthy appearance to the hair, optionally while avoiding or minimizing damage to the hair.

According to various embodiments, methods according to the disclosure may comprise applying a system or composition comprising the system to keratinous substrates, the system comprising: at least one active agent, at least one acid free of carbon-carbon double bonds; and optionally at least one cationic polymer; and applying to the keratinous substrates a composition for coloring or lightening the hair, said composition comprising: an oxidizing composition, and optionally, at least one colorant composition; wherein the system or composition comprising the system is substantially free of crosslinking agents; and wherein the system or composition comprising the system is applied to the hair before, after, or at the same time as the composition for coloring or lightening the hair is applied to the hair.

According to various embodiments, methods according to the disclosure may comprise applying to keratinous substrates a system or composition comprising the system comprising: at least one active agent; at least one acid free of carbon-carbon double bonds; and optionally at least one cationic polymer; wherein the system and/or composition comprising the system is substantially free of crosslinking compounds.

In other embodiments, the disclosure is directed to a method for the treatment of keratinous substrates comprising: applying a system or composition comprising the system to the keratinous substrates, the system comprising: at least one active agent; at least one acid free of carbon-carbon double bonds; optionally at least one cationic polymer; and applying to the keratinous substrates a composition for coloring or lightening the hair, said composition comprising: an oxidizing composition, and optionally, at least one colorant composition; wherein the system and/or composition comprising the system is substantially free of crosslinking compounds; and wherein the system or composition comprising the system is applied to the hair before, after, or at the same time as the composition for coloring or lightening the hair is applied to the hair.

In other embodiments, the disclosure is directed to a method for the treatment of keratinous substrates comprising: applying a system or composition comprising the system to the keratinous substrates, the system comprising: at least one active agent; at least one acid free of carbon-carbon double bonds; optionally at least one cationic polymer; and applying to the keratinous substrates a composition for relaxing, straightening, perming, or waving the hair, said composition comprising at least one agent for relaxing, straightening, perming, or waving the hair; wherein the system and/or composition comprising the system is substantially free of crosslinking compounds; and wherein the system or composition comprising the system is applied to the hair before, after, or at the same time as the composition for relaxing, straightening, perming, or waving the hair is applied to the hair.

According to various embodiments, kits for altering the color of hair may comprise: a first compartment containing a system or composition comprising the system comprising: at least one active agent; at least one acid free of carbon-carbon double bonds; and optionally at least one cationic polymer, wherein the system is free or substantially free of crosslinking agents; a second compartment containing an oxidizing composition, and optionally, a third compartment containing at least one coloring component.

According to various embodiments, kits for altering the shape of hair may comprise: a first compartment containing a system or composition comprising the system comprising: at least one active agent; at least one acid free of carbon-carbon double bonds; and optionally at least one cationic polymer, wherein the system is free or substantially free of crosslinking agents; a second compartment containing at least one agent for relaxing, straightening, perming, or waving the hair, and optionally, a third compartment containing at least one neutralizing agent, e.g., neutralizing liquid.

BRIEF DESCRIPTION OF THE DRAWINGS

The present disclosure and claims can be better understood from the following detailed description either alone or together with the accompanying drawings. The drawings are included to provide a further understanding, and are incorporated in and constitute a part of this specification. The drawings illustrate one or more exemplary embodiments of the present disclosure and together with the description serve to explain various principles and operation.

DETAILED DESCRIPTION

Figure 1:
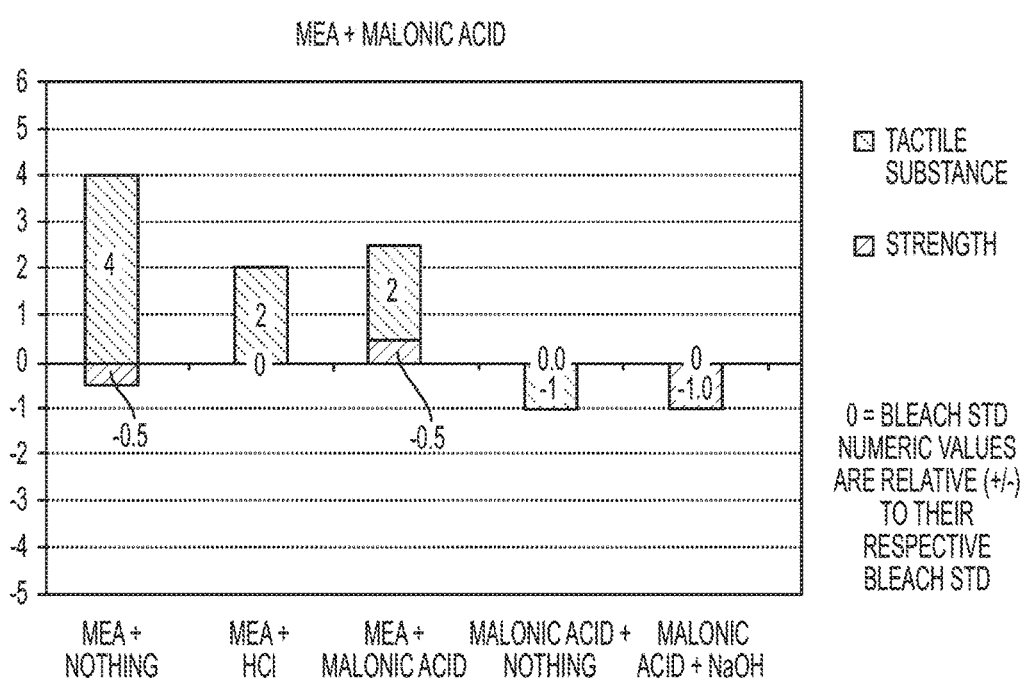
FIG. 1 shows sensorial comparison for MEA and malonic acid.

Other than in the operating examples, or where otherwise indicated, all numbers expressing quantities of ingredients and/or reaction conditions are to be understood as being modified in all instances by the term "about" which can encompass ±10%, ±8%, ±6%, ±5%, ±4%, ±3%, ±2%, ±1%, or ±0.5%.

All numbers expressing pH values are to be understood as being modified in all instances by the term "about" which encompasses up to +3%.

"At least one" as used herein means one or more and thus includes individual components as well as mixtures/combinations.

"Keratinous substrate" may be chosen from, for example, human hair.

"Chemical treatment" as described herein may include any chemical treatment, such as by way of non-limiting example only, oxidation dyeing, coloring, lightening (e.g., bleaching, highlighting) relaxing, perming, waving, and/or straightening the hair.

"Systems" as used herein are meant to include compositions comprising at least one active agent and at least one acid. Optionally, the systems may comprise additional components as described herein.

The term "altering the color" or "color-altering" as used herein may refer to lifting or lightening the color of hair. It can also refer to dyeing or coloring hair or depositing color onto the hair. In certain instances, it refers to lifting or lightening the color of hair and depositing color onto the hair at the same time.

The term "strength" as used herein may refer to the strength of the hair fiber with respect to the ease or difficulty of breaking a hair fiber or to the amount of effort or force needed to break the fiber when the fiber is subjected to a pulling, tugging, stretching, combing, or brushing action.

The term "protecting" as used herein may refer to the prevention, minimization or reduction of damage or further damage to hair.

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Polymers," as defined herein, include homopolymers and copolymers formed from at least two different types of monomers.

"(Meth)acrylic" as used herein, is understood to mean, within the meaning of the present patent application, "acrylic or methacrylic".

The term "substantially free of (a component)" as defined herein means that the systems or compositions contain no appreciable amount of the component, for example, no more than about 1% by weight, or no more than about 0.5% by weight, or no more than about 0.3% by weight, such as no more than about 0.1% by weight, based on the weight of the system or composition comprising the system and/or the oxidizing composition according to embodiments of the disclosure.

The term "free" or "completely free of (a component)" as defined herein means that the systems or compositions do not contain the component in any measurable degree by standard means.

As used herein, the term "crosslinking agent" may refer to any traditional crosslinking compound, such as those that can crosslink free thiol compounds, for example bis-maleimido compounds.

Systems

It has been surprisingly and unexpectedly discovered that when keratinous substrates, e.g., hair, are treated with systems (also referred to as "treatment systems" or "treatment compositions") comprising at least one active agent and at least one acid according to various embodiments of the disclosure before, during, and/or after chemical treatment, improved effects such as, for example, improved fiber strength and/or protecting and/or coloring/lightening effects can be achieved. According to at least certain embodiments of the disclosure, it has been discovered that by using the systems described herein, the level of cysteic acid in the hair was reduced by about 15% compared to hair treated by similar methods but without the featured systems.

Without wishing to be bound by theory, it is believed that the active agent may form ionic bonds with a negatively charged moiety on the keratinous substrate, which in turn can create bonds between pairs of negatively charged moieties, thereby strengthening and imparting beneficial cosmetic properties to the keratinous substrate (e.g., softening, strengthening, protecting, etc., the hair).

In addition, in at least certain embodiments, the system may lower the oxidation or reduction process on the disulfide bonds in keratinous substrates, and therefore protect the keratinous substrate. For example, several active agents can rearrange themselves in order to create a three dimensional (3D) structure that can act as a chelating agent, blocking some metal ions naturally present in the hair fiber (when these metal ions are present and free within the hair fiber, these metals catalyze the oxidation processes and form cysteic acid). Thus, a reduction in the amount of cysteic acid indicates an improvement in the cosmetic properties of the hair (e.g., integrity, hair strength, and the like).

In certain embodiments, the diamines of the systems can act as an alkaline agent, assisting in the lightening of the hair fiber.

In various, non-limiting examples, the systems or compositions comprising the systems may have a pH of less than or equal to about 11, such as less than or equal to about 10.5, less than or equal to about 10.3, less than or equal to about 10.1, less than or equal than about 10.0, less than or equal to about 9.9, or less than or equal to about 9.8. For example, the pH may range from about 7 to about 11, such as from about 7.5 to about 10.5, such as from about 8 to about 10.3, or such as from about 8.5 to about 10. In further embodiments, the pH may range from about 9.5 to about 10.5, about 9.7 to about 10.4, about 9.9 to about 10.3, or about 10 to about 10.2. In one embodiment, the pH may be about 10.1.

In other various, non-limiting examples, the systems or compositions comprising the systems may have a pH of equal to or greater than about 12 or equal to or greater than about 13, and can range from about 12.5 to about 14, or preferably from about 13 to about 14, or more preferably from about 13.2 to about 13.8, or even more preferably from about 13.5 to about 13.7, including all ranges and subranges therebetween.

In yet other various, non-limiting examples, the systems or compositions comprising the systems may have a pH of less than or equal to about 7, such as from about pH 2 to less than about 7, preferably, from about pH 2 to about 6.5, or more preferably from about pH 2 to about 6 or from about pH 2 to about 4, including all ranges and subranges therebetween.

The pH of the systems or compositions comprising the systems of the present disclosure may be adjusted to the desired value using conventional acidifying or basifying agents.

The pH of all numbers expressing pH values are to be understood as being modified in all instances by the term "about," which encompasses up to +/−1% of the indicated pH value (e.g. "about 12.2" means 12.125-12.32 and "about 2" means 1.8-2.2).

In one embodiment, the system or compositions comprising the systems may be buffered, for example by using citric acid, or a combination of glycine and hydrochloric acid.

In at least certain embodiments, the systems or compositions comprising the systems are free or substantially free of crosslinking agents.

Active Agents

The systems or composition comprising the systems can comprise at least one active agent. According to various embodiments, the at least one active agent will be chosen according to pKa, in order to have some positive charge in the usage conditions. It is within the ability of one of skill to choose an active agent in order to have some positive charge in the systems and compositions described herein. For example, the active agent can have a pKa ranging from about 8.5 to about 10.5, ranging from about 9.0 to about 10.25, or ranging from about 9.5 to about 10.

Without wishing to be bound by theory, choosing the at least one active agent having a pKa to allow it to be positively charged in the systems and compositions described herein may allow for the formation of ionic bonds with any negatively charged moiety available in the hair fiber, such as $SO_3^-$, $CO_2^-$, and therefore create bonds between each pair of negative moieties. In this regard, it may be advantageous in at least certain embodiments to choose the at least one active agent so that the length/size or molecular weight of the molecule is not too great or too small, so that the molecules are able to diffuse within the hair fiber and to create the bonds between two negatively charged moieties.

Suitable active agents include, for example, those of formula (I):

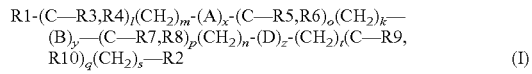
(I)

wherein:
R1 and R2 are independently chosen from alkyl, hydrogen, hydroxyl, methoxy, ethoxy, or amine;
R3, R4, R5, R6, R7, R8, R9, R10 are independently chosen from side hydrogen, alkyl chains, hydroxyl, methoxy, ethoxy, or amine;
A and B and D are independently chosen from ethylene oxide, propylene oxide, butyleneoxide, isopropylene oxide, isobutylene oxide groups, or NH, alkyl amine, dialkyl amine;
k, l, m, n, o, p, q, s, t are independently chosen from integers ranging from 0 to 20;
x and y, z are independently chosen from integers ranging from 0 to 20.

Suitable active agents also include those of formula (II):

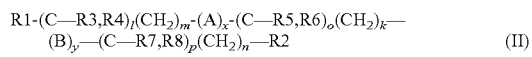
(II)

wherein:
R1 and R2 are independently chosen from alkyl, hydrogen, hydroxyl, methoxy, ethoxy, or amine;
R3, R4, R5, R6, R7, R8 represent side hydrogen, alkyl chains, hydroxyl, methoxy, ethoxy, or amine;
A and B and are independently chosen from ethylene oxide, propylene oxide, butyleneoxide, isopropylene oxide, isobutylene oxide groups, or NH, alkyl amine, dialkyl amine;
k, l, m, n, o, p, are independently chosen from integers ranging from 0 to 20; and
x and y are independently chosen from integers ranging from 0 to 20.

Exemplary active agents of formulae (I) and (II) may be chosen from, but are not limited to: 2-dimethylamino; dimethylamine; triamine bis(hexamethylene)triamine; polyoxypropylene monoamine; polyoxypropylene diamine; polyoxyethylene/polyoxypropylene monoamine; polyoxyethylene diamine, polyoxypropylene monoamine, n,n-dimethylhexylamine, trimethylammonio, 2,2-bis(aminoethoxy)propane, meso-1,4-diamino-2,3-butanediol dihydrochloride, 1,5-diamino-2-methylpentane, 1,2-diaminopropane, 1,3-diaminopentane, (3s,4s)-(−)-3,4-hexanediamine dihydrochloride, tris[2-(2-methoxyethoxy)ethyl]amine, and combinations thereof.

Suitable active agents also include those of formula (III):

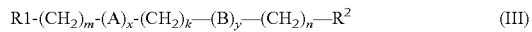
(III)

wherein:
R1 and R2 represent alkyl, hydroxyl, or amine;
A and B are independently chosen from ethylene oxide, propylene oxide, butylene oxide, isopropylene oxide, isobutylene oxide groups;
k, n, m are independently chosen from integers ranging from 0 to 20;
x and y are independently chosen from integers ranging from 0 to 20.

Exemplary active agents of formula (III) may be chosen from, but are not limited to: ethanolamine (MEA); 2-aminoethanol; 3-butoxypropylamine; 3-ethoxypropylamine; tetradecylamine; 1,9-Diaminononane; 4,9-Dioxa-1,12-dodecanediamine; 4,7,10-Trioxa-1,13-tridecanediamine; Ethylenediamino; N-(2-Hydroxyethyl)ethylenediamine; triethylene glycol diamine; 1,11-Diamino-3,6,9-trioxaundecane; 1,3-Diaminopropane; 1,4-Diaminobutane; 1,5-Diaminopentane; 1,6-Diaminohexane; 1,7-Diaminoheptane; 3-(octyloxy)propan-1-amine, and combinations thereof.

In yet further exemplary and non-limiting embodiments, the active agent can be chosen from guanadine hydrochloride; polyoxypropylene triamine; crown ethers, such as 1,4,7,10-tetraoxacyclododecane; 4,7,13,16,21,24-hexaoxa-1,10-diazabicyclo[8.8.8]-hexacosane; and combinations thereof.

Suitable active agents can include, for example, diamines. Non-limiting examples of diamines that may be useful according to various embodiments may be primary amines and secondary amines. The diamine can include both primary and secondary amine groups in various exemplary embodiments. In at least one embodiment, the diamine contains only primary amine groups.

Optional diamines may include at least one ethylene oxide group according to various embodiments. For example, between 1 and 4 ethylene oxide groups can be present in the diamine. The diamine may optionally include propylene oxide groups. For example, between 1 and 4 propylene oxide groups can be present in the diamine.

Without wishing to be limited, exemplary diamines include 4,9-dioxadodecane-diamine; 4, 7, 10-trioxa-1,13-tridecanediamine; ethylenediamino; polyoxypropylene diamine; polyethylene glycol diamine; triethylene glycol diamine (2OE); n-(2-hydroxyethyl)-ethylenediamine; 1,3-diaminopropane; 1,7-diaminoheptane; 1,4-diaminobutane; 1,2-diaminopropane; 1,6-diaminohexane; 1,11-diamino-3,6,9-trioxaundecane; 1,5-diaminopentane; polyoxyethylene diamine; 2,2-dimethyl-1,3-propanediamine; 2,2-bis(aminoethoxy)propane; 4,7,10-trioxa-1,13-tridecanediamine; 1,3-diaminopentane; 4,7,10-trioxa-1,13; 1,5-diamino-2-methylpentane; (3s,4s)-(−)-3,4-hexanediamine dihydrochloride; 1,9-diaminononane, and mixtures thereof.

According to one embodiment, the diamine is not chosen from ethylenediamino; 1,6-diaminohexane; 4,7,10-trioxa-1,13; 1,5-diamino-2-methylpentane; or triethylene glycol diamine (2OE).

The active agent can have a molecular weight of less than about 1000, such as less than about 500, such as less than about 350, such as less than about 250, according to at least some embodiments.

The at least one active agent can be present in an amount ranging from about 0.1% to about 20%, by weight based on the total weight of the system or composition comprising the system in which it is present. For example, the at least one active agent may be present in an amount ranging up to about 10%, such as from about 1% to about 8%, about 3% to about 6%, or about 4% to about 5%, by weight based on the total weight of the system or composition comprising the system in which it is present. In yet a further embodiment, the at least one active agent can be present in an amount less than about 7%, by weight based on the total weight of the system or composition comprising the system. In yet a further embodiment, the at least one active agent can be present in an amount greater than about 4%, by weight based on the total weight of the system or composition comprising the system.

Acids

The systems according to various embodiments comprise at least one acid. The pKa of the acid can be less than or equal to about 5, such as less than or equal to about 4, or less than or equal to about 3. In at least one embodiment, the pKa of the acid is less than about 2.

Exemplary acids useful according to various embodiments include, without limitation, amino acids, citric acid, hydrochloric (HCl) acid, phosphoric acid, carbonic acid, acetic acid, glycolic acid, lactic acid, tartaric acid, citric acid, malonic acid, malic acid, glucuronic acid, acidic plant extracts, and the salt of these acids, and mixtures thereof.

The at least one acid may be present in an amount ranging from about 0.1% to about 20%, by weight, based on the total weight of the system or composition comprising the system in which it is present. For example, the acid may be present in an amount ranging from about 1% to about 15%, or about 5% to about 12%, by weight, based on the total weight of the system or composition comprising the system in which it is present. In one exemplary embodiment, the acid may be present in an amount of less than about 25%, and in another embodiment, may be present in an amount greater than about 7%, by weight, based on the total weight of the system or composition comprising the system in which it is present.

According to various embodiments of the disclosure the acid may be free or substantially free of carbon-carbon double bonds. By way of non-limiting example, in certain embodiments of the disclosure, e.g. where the systems are free or substantially free of a crosslinking agent, the acid may be free or substantially free of carbon-carbon double bonds.

According to at least one exemplary embodiment, the system can be buffered.

According to various embodiments, when the active agent of formulae (I), (II), or (III) is ethylenediamino; 1,6-diaminohexane; 4,7,10-trioxa-1,13-tridecanediamine; 1,5-diamino-2-methylpentane; or triethylene glycol diamine (2OE), the at least one acid is free of carbon-carbon double bonds.

Solvent

The systems may optionally further comprise solvents. In various exemplary and non-limiting embodiments, the solvent is chosen from cosmetically acceptable solvents. The cosmetically acceptable solvents may be chosen from water, at least one cosmetically acceptable organic solvent, and mixtures thereof.

The organic solvents may be volatile or non-volatile compounds. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, and glycerin.

The cosmetically acceptable solvent may comprise an amount ranging up to about 80%, such as up to about 60%, or from about 5% to about 50% by weight, from about 5% to about 30% by weight, from about 5% to about 25% by weight, or from about 5% to about 20% by weight, based on the total weight of the system or composition comprising the system in which it is present.

Cationic Polymer

The systems according to various embodiments may optionally further comprise cationic polymers. As used herein, a "cationic polymer" is any polymer containing cationic groups and/or groups which can be ionized to cationic groups. Useful cationic polymers can include polyamine, polyaminoamide and quaternary polyammonium polymers, for example.

The polyamine, polyaminoamide and quaternary polyammonium polymers that can be used in the composition of the present invention are described, for example, in French patents FR 2 505 348 and FR 2 542 997. These polymers include the following:

(1) homopolymers or copolymers derived from esters or amides of acrylic or methacrylic acid;

(2) cationic cellulose derivatives such as:

(a) the cellulose ether derivatives containing quaternary ammonium groups that are described, for example, in French patent FR 1 492 597;

(b) the copolymers of cellulose or cellulose derivatives grafted with a water-soluble quaternary ammonium monomer, which are described, for example, in U.S. Pat. No. 4,131,576, such as hydroxyalkylcelluloses, for instance hydroxymethyl-, hydroxyethyl- or hydroxypropyl celluloses grafted in particular with a methacryloylethyltrimethyl-ammonium, methacrylamidopropyltrimethyl-ammonium or dimethyldiallylammonium salt; an example that may be mentioned is polyquaternium 10 (INCI name);

(3) other cationic polysaccharides such as those described, for example, in U.S. Pat. Nos. 3,589,578 and 4,031,307, such as guar gums containing cationic trialkylammonium groups;

(4) polymers composed of piperazinyl units and divalent alkylene or hydroxyalkylene groups having straight or branched chains which are optionally interrupted by oxygen, sulphur or nitrogen atoms or by aromatic or heterocyclic rings, and also the oxidation and/or quaternization products of these polymers. Polymers of this kind are described, for example, in French patents FR 2 162 025 and FR 2 280 361;

(5) polyaminoamides which are soluble in water, such as those described in French patents FR 2 252 840 and FR 2 368 508;

(6) polyaminoamide derivatives, for example, the adipic acid/dialkylaminohydroxy-alkyldialkylenetriamine polymers in which the alkyl group contains 1 to 4 carbon atoms and is preferably a methyl, ethyl or propyl group, and the alkylene group contains 1 to 4 carbon atoms and is preferably the ethylene group. Polymers of this kind are described, for example, in French patent FR 1 583 363;

(7) polymers obtained by reacting a polyalkylene-polyamine containing two primary amine groups and at least one secondary amine group with a dicarboxylic acid selected from diglycolic acid and saturated aliphatic dicarboxylic acids having 3 to 8 carbon atoms. The molar ratio of the polyalkylene-polyamine to the dicarboxylic acid is between 0.8:1 and 1.4:1, and the resulting polyaminoamide is reacted with epichlorohydrin in a molar ratio of epichlorohydrin to the secondary amine group of the polyaminoamide of between 0.5:1 and 1.8:1. Polymers of this kind are described, for example, in U.S. Pat. Nos. 3,227,615 and 2,961,347;

(8) alkyldiallylamine or dialkyldiallylammonium cyclopolymers such as the homopolymer of dimethyl-diallylammonium chloride, and the copolymers of diallyldimethylammonium chloride and acrylamide;

(9) quaternary diammonium polymers having a number-average molecular mass of generally between 1000 and 100 000, such as those described, for example, in French patents FR 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020; an example that may be mentioned is hexadimethrine chloride (INCI name), sold by Chimex under the name Mexomere PO;

(10) quaternary polyammonium polymers such as those described, for example, in patent application EP-A-122 324;

(11) quaternary vinylpyrrolidone and vinylimidazole polymers such as, for example, the products sold under the names Luviquat® FC 905, FC 550 and FC 370 by BASF;

(12) polyamines such as Polyquart® H sold by Henkel, listed under the name "POLYETHYLENE GLYCOL (15) TALLOW POLYAMINE" in the CTFA dictionary; and

(13) crosslinked polymers of methacryloyloxyalkyl($C_1$-$C_4$) trialkyl($C_1$-$C_4$) ammonium salts, such as those sold under the name Salcare® SC 92, Salcare® SC 95 and Salcare® SC 96 by Allied Colloids.

Other cationic polymers which can be used in the context of the invention are cationic proteins or hydrolysates of cationic proteins, polyalkyleneimines, especially polyethyleneimines, polymers containing vinylpyridine or vinylpyridinium units, condensates of polyamines and epichlorohydrin, quaternary polyureylenes and chitin derivatives.

The cationic polymers may optionally be selected from polymers as defined in points (8) and (9), such as hexadimethrine chloride and the homopolymers or copolymers of dimethyldiallylammonium chloride. According to one embodiment, the cationic polymer is hexadimethrine chloride. Mixtures of cationic polymers may also be chosen.

The cationic polymer or polymers, when present, may be present in an amount up to about 50%, such as from about 0.01% to 40%, from about 0.1% to 30%, from about 1% to 20%, or from about 2% to 10%, by weight, relative to the total weight of the system or composition comprising the system.

Compositions

As described above, it may be advantageous to use the systems comprising at least one active agent and at least one acid in conjunction with compositions for chemically treating the hair, such as, for example, hair coloring or hair lightening ("color-altering") compositions. The systems may provide additional advantages in combination with, or in, such compositions. For example, in at least one embodiment, the active agent may have the ability to react in the compositions as alkaline agent, and therefore to lighten the hair fiber. In further exemplary and non-limiting embodiments, the systems can be incorporated into compositions for perms, relaxers, waves, straighteners, primers, shampoos, conditioners, styling compositions such as gels and mousses, holding sprays, BBB sprays, and other keratin treatments.

Accordingly, the above-described systems may be incorporated into cosmetic compositions, for example, hair coloring and/or hair lightening compositions, shampoo compositions, hair conditioning compositions, pre- and post-treatment compositions intended to be applied to the hair before or after chemical treatment such as coloring, bleaching, perming, chemical straightening, etc., and the like. In yet a further embodiment, the systems themselves may optionally further comprise chemical treatment components, for example at least one colorant compound, at least one neutralizing agent, at least one nonionic surfactant, and/or at least one auxiliary agent suitable for use in cosmetic compositions, such as chelating agents and strengthening agents. It is to be understood that the systems may be incorporated into cosmetic compositions, or the systems themselves may be cosmetic compositions that further comprise chemical treatment components, without limitation thereto.

By way of non-limiting example, the above-described systems may thus optionally be mixed with an oxidizing composition containing at least oxidizing agent selected from peroxides, urea peroxide, alkali metal bromates, ferricyanides, peroxygenated salts, perborates, percarbonates, laccases, peroxidases, redox enzymes, and mixtures thereof, and a cosmetically acceptable solvent selected from water and a water/organic solvent mixture. The resulting composition comprising the system and the oxidizing composition may be useful for lifting or lightening the color of the hair. When the cosmetic composition additionally contains a colorant compound, the resulting composition may be useful for depositing color onto hair.

In yet a further non-limiting example, the above-described systems may optionally be mixed with hair styling agents such as permanent waving, relaxing, or straightening agents. Such hair styling agents may optionally be chosen from inorganic hydroxides or organic hydroxides, for example sodium hydroxide, potassium hydroxide, lithium hydroxide, calcium hydroxide, or guanidine hydroxide, or may be chosen from organic amines and other non-hydroxide compounds. In various embodiments, the hair relaxing agents may be chosen from thiol compounds such as cysteine, cysteamine, N-substituted cysteamines, alkyl substituted mercaptoacetamides, dimercaptoadipic acid, thioglycerol, thiolactic acid, thioglycolic acid or its salts, (e.g., a thioglycolate), monothioglycolic acid esters such as diol esters of thioglycolic acid, glyceryl monothioglycolate, thiocholine or its salts, amino thiols, and thiols attached to low molecular weight polymers, sulfites such as sodium hyposulfite, and bisulfites such as ammonium or sodium bisulfite. The resulting compositions comprising the system and the hair styling agents may be useful for permanent waving, relaxing, or straightening the hair, for example.

Colorants

As described herein, in one exemplary and non-limiting embodiment, a cosmetic composition comprising the system, or the system itself, may optionally comprise at least one colorant compound chosen from oxidative dye precursors, direct dyes, pigments, and mixtures thereof.

The oxidation dyes are generally chosen from one or more oxidation bases optionally combined with one or more couplers.

By way of example, the oxidation bases may be chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β- hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N-bis(4'-aminophenyl)-1,3-diaminopropanol, N,N'-bis(p-hydroxyethyl)-N,N-bis(4'-aminophenyl)ethylenediamine, N,N'-bis(4-aminophenyl)tetramethylenediamine, N,N'-bis(β-hydroxyethyl)-N,N-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases can include the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-□-hydroxyethoxy-3-amino-pyrazolo[1,5-a]pyridine; 2-(4-diméthylpyperazinium-1-yl)-3-amino-pyrazolo[1,5-a]pyridine; and the addition salts thereof.

More particularly, oxidation bases can be selected from 3-aminopyrazolo-[1,5-a]-pyridines and preferably substituted on carbon atom 2 by:

(a) one (di)($C_1$-$C_6$)(alkyl)amino group wherein said alkyl group can be substituted by at least one hydroxy, amino, imidazolium group;

(b) one heterocycloalkyl group containing from 5 to 7 members chain, and from 1 to 3 heteroatomes, potentially cationic, potentially substituted by one or more ($C_1$-$C_6$) alkyl, such as di($C_1$-$C_4$)alkylpipérazinium; or (c) one ($C_1$-$C_6$)alkoxy potentially substituted by one or more hydroxy groups such as α-hydroxyalkoxy, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazino-pyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-((3-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof 4,5-Diamino-1-(β-methoxyethyl)pyrazole may also be used.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]

pyrazol-1-one, 2-amino-3-dimethylamino-6,7-dihydro-1H, 5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1, 2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Compositions and/or systems according to embodiments of the disclosure may optionally further comprise one or more couplers advantageously chosen from those conventionally used in the dyeing or coloring of keratinous substrates.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzo-morpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

The oxidation base(s) may be present in an amount ranging from about 0.001% to 10% by weight, such as from about 0.005% to 5% by weight, relative to the total weight of the system or composition comprising the system in which it is present.

The coupler(s), if they are present, may be present in an amount ranging from about 0.001% to 10% by weight, such as from about 0.005% to 5% by weight, relative to the total weight of the system or composition comprising the system in which it is present.

Compositions according to embodiments of the disclosure may optionally comprise one or more synthetic or natural direct dyes, for example chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Preferably direct dyes are cationic direct dyes. Mention may be made of the hydrazono cationic dyes of formulas (Va) and (V'a), the azo cationic dyes (VIa) and (VI'a) and the diazo cationic dyes (VIIa) below:

  (Va)

  (V'a)

  (VIa)

  (VI'a)

and

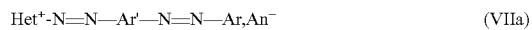  (VIIa)

in which formulas (Va), (V'a), (VIa), (VI'a) and (VIIa):

Het$^+$ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar$^+$ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy;

Ar" is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

—R$^a$ and R$^b$, which may be identical or different, represent a hydrogen atom or a group ($C_1$-$C_8$)alkyl, which is optionally substituted, preferentially with a hydroxyl group; or alternatively the substituent R$^a$ with a substituent of Het$^+$ and/or R$^b$ with a substituent of Ar and/or R$^a$ with R$^b$ form, together with the atoms that bear them, a (hetero)cycloalkyl;

particularly, R$^a$ and R$^b$ represent a hydrogen atom or a group ($C_1$-$C_4$)alkyl, which is optionally substituted with a hydroxyl group;

An$^-$ represents an anionic counter-ion such as mesylate or halide.

In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954.

Preferentially, the cationic part is derived from the following derivatives:

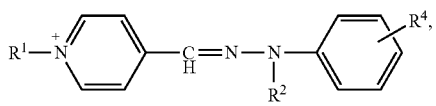

(Va-1)

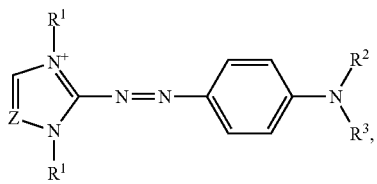

(VIa-1)

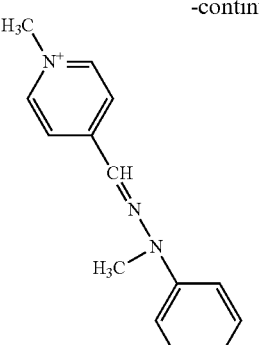

Basic Yellow 87 formulae (V-1) and (VI-1) with:
  R' representing a $(C_1-C_4)$ alkyl group such as methyl;
  $R^2$ and $R^3$, which are identical or different, represent a hydrogen atom or a $(C_1-C_4)$alkyl group, such as methyl; and
  $R^4$ represents a hydrogen atom or an electron-donating group such as optionally substituted $(C_1-C_8)$alkyl, optionally substituted $(C_1-C_8)$alkoxy, or $(di)(C_1-C_8)$(alkyl)amino optionally substituted on the alkyl group(s) with a hydroxyl group; particularly, $R^4$ is a hydrogen atom,
  Z represents a CH group or a nitrogen atom, preferentially CH;
  An⁻ represents an anionic counter-ion such as mesylate or halide.

The dye of formulae (Va-1) and (VIa-1) can be chosen from Basic Red 51, Basic Yellow 87 and Basic Orange 31 or derivatives thereof:

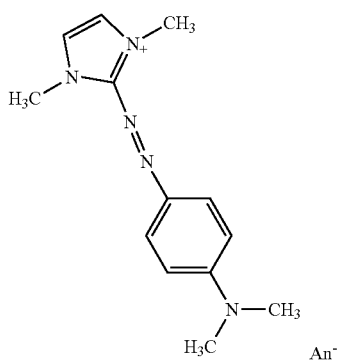

Basic Red 51

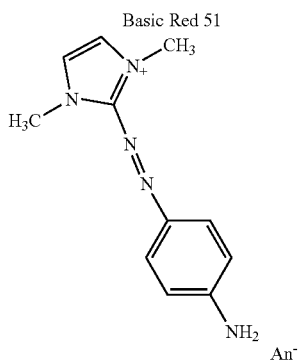

Basic Orange 31

Among the natural direct dyes, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the one or more direct dyes more particularly represent from about 0.001% to 10% by weight, such as from about 0.005% to 5% by weight, of the total weight of the system or composition comprising the system in which it is present.

Nonionic Surfactants

The cosmetic compositions or systems according to various embodiments may further optionally comprise at least one nonionic surfactant. In general, nonionic surfactants having a Hydrophilic-Lipophilic Balance (HLB) of from 8 to 20, may be used. Non-limiting examples of nonionic surfactants useful in the compositions are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, preferably in the $C_{16}$-$C_{40}$ range, more preferably in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from Uniqema, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij® 72 (i.e., Steareth-2) and Brij® 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. These compounds can be represented by the formula (S)n-O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$-$C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, preferably glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. For example, nonionic surfactants can include sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Uniqema, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. According to certain embodiments, sorbitan monoisostearate and sorbitan sesquioleate can be used as emulsifiers.

Also suitable for use herein are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to about 20).

The nonionic surfactant(s) for use in the compositions can be different than the above-described fatty substance(s) employed in said compositions.

The nonionic surfactants are those formed from a fatty alcohol, a fatty acid, or a glyceride with a $C_4$ to $C_{36}$ carbon chain, a $C_{12}$ to $C_{18}$ carbon chain, a $C_{16}$ to $C_{18}$ carbon chain, derivatized to yield an HLB of at least 8. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 8. The nonionic surfactants can contain ethoxylate in a molar content of from 10-25, or from 10-20 moles.

The nonionic surfactant, if present, may be present in an amount ranging from about 0.1% to about 30% by weight, such as from about 0.5% to 20% by weight, from about 1% to about 10% by weight, or from about 1% to about 5% by weight, based on the total weight of the system or composition comprising the system in which it is present.

Oxidizing Agents

Various exemplary and non-limiting compositions and systems according to embodiments of the disclosure can optionally include an oxidizing composition comprising at least one oxidizing agent which may be chosen, for example, from peroxides, persulfates, perborates percarbonates, alkali metal bromates, ferricyanides, peroxygenated salts, or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In one embodiment, the oxidizing agent can be hydrogen peroxide present in an aqueous solution whose titre may range from 1 to 40 volumes, such as from 5 to 40 volumes or such as from 5 to 20 volumes.

In another embodiment, the oxidizing agent can be a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof.

In certain embodiments, the oxidizing agent is hydrogen peroxide.

In general, the oxidizing agent will be present in an amount ranging from about 0.05 to about 50% by weight, such as from about 0.1% to about 30% by weight, from about 0.1% to about 20% by weight, or from about 1% to about 10% by weight, based on the total weight of the oxidizing composition or solution or system in which it is present.

In one particular embodiment, the oxidizing composition is aqueous or is in the form of an emulsion.

In another embodiment, the oxidizing composition is substantially anhydrous.

The term "substantially anhydrous" means that the oxidizing composition is either completely free of water or contains no appreciable amount of water, for example, no more than 5% by weight, or no more than 2% by weight, or no more than 1% by weight, based on the weight of the oxidizing composition. It should be noted that this refers for example to bound water, such as the water of crystallization of the salts or traces of water absorbed by the raw materials used in the preparation of the compositions according to embodiments of the disclosure.

The oxidizing composition can contain at least one solvent, chosen from water, organic solvents, and mixtures thereof.

When the oxidizing composition is substantially anhydrous, the oxidizing composition may comprise at least one solvent chosen from organic solvents.

Suitable organic solvents for use in the oxidizing composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The organic solvents for use in the present invention can be volatile or non-volatile compounds.

The organic solvent may, for example, be present in an amount ranging from about 0.5% to about 70% by weight, such as from about 2% to about 60% by weight, preferably from about 5 to about 50% by weight, relative to the total weight of the oxidizing composition or system in which it is present.

The oxidizing composition may be in the form of a powder, gel, liquid, foam, lotion, cream, mousse, and emulsion.

The oxidizing composition can also be called a developer composition.

The oxidizing composition of the present invention may also contain at least one fatty substance as described above. Thus, the total amount of fatty substances in the combination or mixture of the cosmetic and oxidizing compositions of the present invention may range from about 10% to about 80% by weight, or such as from about 20% to about 60% by weight, or such as from about 20% to about 40% by weight, or such as from about 20% to about 30% by weight, based on the total weight of the composition or system in which it is present.

The pH of the oxidizing composition can range from about 2 to about 12, such as from about 6 to about 11, and it may be adjusted to the desired value using acidifying/alkalizing agents that are well known in the art. In certain embodiments, the pH of the oxidizing composition is below 7.

The pH of the composition resulting from mixing together the system and the oxidizing composition may range from about 2 to about 7, such as from about 3 to about 6.9, or from about 4 to about 6.9, or from about 4 to about 6.85, or from about 5 to about 6.8.

According to at least one embodiment, the system and/or compositions comprising the system and the oxidizing composition are free or substantially free of ammonia.

Auxiliary Agents

The system or composition comprising the system may further optionally comprise at least one auxiliary agent suitable for use in cosmetic compositions. The auxiliary agent may include, but is not limited to thickening agents and rheology modifying agents, cationic polymers, film forming compounds, humectants and moisturizing agents, chelating agents such as glycine, emulsifying agents other than those that fall under the above-described fatty substances, fillers, structuring agents, propellants, anionic surfactants, cationic surfactants, amphoteric surfactants, shine agents, conditioning agents, shine agents, and strengthening agents. For example, the at least one auxiliary agent may be chosen from but not limited to, Polyquaternium-34, SAMSON Supplied by Ashland, N-Hance 4572 supplied by Ashland, N-Dur-Hance A1000 supplied by Ashland, Merquat 100 supplied by Lubrizol, Merquat 2003 supplied by Lubrizol, Belsil ADM 8301 E supplied by Wacker, (ShineE503713) supplied by Wacker, Filoxane, cerafill, wheat amino acid proteins, Glycerin, ceramide, threonine.

Thickening agents and rheology modifying polymers may be chosen from polymeric thickeners and non-polymeric thickeners. The polymeric thickener can be chosen from ionic or non-ionic, associative or non-associative polymers. Exemplary polymeric thickeners include various native gums. Representative non-polymeric thickening agents include oxyethylenated molecules and especially ethoxylated alkyl or acyl derivatives of polyols. These polymers can optionally be modified physically or chemically.

If present, the at least one auxiliary agent may be present in an amount up to about 25%, such as up to about 20%, up to about 15%, or up to about 10% by weight, such as from about 0.1% to about 10% by weight, from about 0.5% to about 5%, or about 1 to about 3% by weight, based on the total weight of the system or composition comprising the system in which it is present.

The compositions and systems according to embodiments of the disclosure can also comprise at least one cosmetically acceptable additive used conventionally in compositions for application onto hair.

"Additive" means a substance that is added, different from the compounds already mentioned.

As examples of cosmetically acceptable additives that can be used, non-limiting mentions can be made of antioxidants or reducing agents, penetrating agents, sequestering agents, perfumes, buffers, dispersants, ceramides, sunscreen agents, preservatives, opacifiers, and antistatic agents.

The systems and/or compositions of the present invention according to the disclosure can be in various forms, such as in the form of liquids, creams, liquid-gels, liquid-creams, gels, lotions or pastes.

The system or composition comprising the system can be included in any hair treatment composition including but not limited to dyes, bleaches, shampoos, conditioners, leave-in hair treatments, masques, relaxers, perms, waves, and straighteners. By way of non-limiting example, a cosmetic composition having a first active agent can be included in hair coloration composition and applied to the hair. Subsequently, the hair may be rinsed, and a shampoo comprising the cosmetic composition having a second active agent can be applied to the hair and rinsed. Next, a conditioner comprising the cosmetic composition having a third active agent can be applied to the hair. Any of the first, second, and third active agents in the exemplary and nonlimiting embodiment described can be the same or different. The shampoo and/or conditioner can also be applied at any other time after chemically treating the hair with a coloring or lightening composition or a hair shaping composition such as a relaxer, straightener, wave or perm.

Processes for Treating Hair

As described herein, the systems and/or cosmetic compositions comprising the systems may be used to treat the hair. In various embodiments, the systems and/or compositions disclosed herein may be used on hair that has not been previously treated, for example has not been previously relaxed, straightened, permed, waved, artificially dyed and/or pigmented. In further embodiments, the systems and/or compositions disclosed herein may be used on hair that has been previously treated, for example not been previously relaxed, straightened, permed, waved, artificially dyed and/or pigmented.

Exemplary processes for treating the hair may comprise applying the systems and/or cosmetic composition onto the hair before, during, or after chemical treatment of the hair, in order to provide shine, conditioning, fiber strength, and/or a healthy appearance to the hair, while avoiding or minimizing damage to the hair.

As used herein, systems and compositions comprising the systems may be applied to the hair "before" chemical treatment of the hair, with or without shampooing or rinsing in between, such as less than one minute before, up to about 5 minutes before, up to about 10 minutes before, up to about 20 minutes before, up to about 30 minutes before, up to about 1 hour before, up to about 2 hours before, up to about 6 hours before, up to about 12 hours before, up to about 24 hours before, up to about 48 hours before, up to about 72 hours before, or up to about 1 week before, for example.

As used herein, systems and compositions comprising the systems may be applied to the hair "after" chemical treatment of the hair, with or without shampooing or rinsing in between, such as less than one minute after, up to about 5 minutes after, up to about 10 minutes after, up to about 20 minutes after, up to about 30 minutes after, up to about 1 hour after, up to about 2 hours after, up to about 6 hours after, up to about 12 hours after, up to about 24 hours after, up to about 48 hours after, up to about 72 hours after, or up to about 1 week after, for example.

As used herein, systems and compositions comprising the systems may be applied to the hair "during" chemical treatment of the hair (e.g. at approximately the same time as), for example by applying the systems as a part of the chemical treatment of the hair (e.g. the system is incorporated into a chemical treatment, such as into a color-altering (e.g. hair dyeing or hair bleaching) or hair relaxing composition, or the chemical treatment is incorporated into the system, such as a hair relaxing agent being mixed into the system), or for example where the system or composition comprising the system is separate from the chemical treatment composition but be applied substantially at the same time as the system or composition comprising the system, with or without shampooing or rinsing in between.

By way of non-limiting example, a process may comprise applying the system or composition onto the hair as a pre-treatment composition, which may optionally be left on the hair or washed out before application of a chemical treatment. In a further exemplary embodiment, a process may comprise adding the system or composition into a chemical treatment composition, e.g., a relaxing, straightening, perming, waving, colorant, or bleach composition, a developer composition, or a mixture thereof, optionally just prior to use, and applying to the hair. In yet a further exemplary embodiment, a process may comprise adding a hair styling agent, for example a hair relaxing, straightening, or permanent waving agent, into a system or composition according to the disclosure, optionally just prior to use, and applying the system to the hair to be treated. In yet a further exemplary embodiment, a process may comprise mixing a colorant or bleach composition and developer just prior to use, wherein the system or composition comprising the system may be pre-formulated into the colorant or bleach composition, or developer composition. In yet a further exemplary embodiment, a process may comprise applying the system or composition comprising the system onto the hair as a post-treatment composition after the hair has been treated, which may optionally be left on the hair or washed out.

The term "mix" and all variations of this term as used herein refers to contacting or combining or reconstituting or dissolving or dispersing or blending or shaking the system or cosmetic composition with the oxidizing composition. It can also mean introducing the system or cosmetic composition to the oxidizing composition. It may also mean placing the cosmetic composition in the same vessel or container as the oxidizing composition.

Upon application of the system or composition comprising the system to the hair, and after an optional resting time (leave-on time) on the hair fibers, for example, ranging from about 1 to about 60 minutes, such as from about 5 to about 45 minutes, or such as from about 5 to about 20 minutes, or such as from about 10 to about 20 minutes, or such as of about 20 minutes, the keratinous substrates are rinsed, optionally washed with shampoo, rinsed again, optionally washed with a hair conditioning composition, and rinsed again, then dried. The shampoo and hair conditioning composition can be any conventional hair shampoo and/or conditioner products, or may optionally be shampoo and/or conditioner products comprising the systems described herein.

The temperature during the process of treating the hair may be, for example, between room temperature and 80° C., such as between room temperature and 60° C.

It has been discovered that the application of the final mixture or composition onto the fibers results in satisfactory lifting or lightening of the color of the fibers, while providing strengthening and/or protection to the hair fiber, so as to avoid or minimize damage to the hair fiber in at least some embodiments. When the embodiments of the composition further comprise a colorant compound selected from oxidative dye precursors, direct dyes, pigments or their mixtures, the fibers are also colored satisfactorily with respect to degree of color deposit and desirable shade formation coloring, while providing strengthening and/or protection to the hair fiber, so as to avoid or minimize damage to the hair fiber in at least some embodiments.

It has also been discovered that the systems and/or cosmetic compositions comprising the at least one active agent and at least one acid free of carbon-carbon double bonds can be used in methods for perming, waving, relaxing, or straightening hair, while providing strengthening and/or protection to the hair fiber, so as to avoid or minimize damage to the hair fiber in at least some embodiments.

It is to be understood, however, that any degree of protection and/or strengthening may be imparted to the hair fiber, without limitation. In addition, it is intended that embodiments that do not impart fiber strength and/or protection to the hair fiber are also within the scope of the disclosure.

Yet further embodiments comprise a kit for chemical treatment of the hair. One embodiment of a kit for altering the color of hair comprises a first compartment containing a system or composition comprising the system comprising:

i. at least one active agent;
ii. at least one acid free or substantially free of carbon-carbon double bonds;
iii. optionally at least one cationic polymer;

wherein the system or composition comprising the system is substantially free of crosslinking compounds; a second compartment containing an oxidizing composition; and optionally, a third compartment comprising at least one colorant or bleaching agent Alternative kits can include a first compartment containing a system or composition comprising the system comprising:
i. at least one active agent;
ii. at least one acid free or substantially free of carbon-carbon double bonds;
iii. optionally at least one cationic polymer;

wherein the system or composition comprising the system is substantially free of crosslinking compounds; a second compartment comprising a perming solution or a waving solution; and a third compartment comprising a neutralizer liquid.

Another exemplary kit can include a first compartment containing a system or composition comprising the system comprising:
i. at least one active agent;
ii. at least one acid free or substantially free of carbon-carbon double bonds;
iii. optionally at least one cationic polymer;

wherein the system or composition comprising the system is substantially free of crosslinking compounds; a second compartment comprising a relaxing or straightening agent; and a third compartment comprising a neutralizer liquid.

An exemplary process can include applying to the hair a system or composition comprising the system for straightening or relaxing or perming or waving the hair, comprising:
i. at least one active agent;
ii. at least one acid free or substantially free of carbon-carbon double bonds;
iii. optionally at least one cationic polymer;

wherein the system or composition comprising the system comprises a hair straightening, relaxing, perming, or waving agent, and is substantially free of crosslinking compounds; and applying heat via a heat source such as a flat iron, curler, hair dryer, and the like, before, during, or after the composition is applied to or in contact with the hair.

An exemplary method can comprise protecting and/or strengthening the hair fiber during, before, or after a chemical treatment, comprising applying to the hair a system or composition comprising the system comprising:
i. at least one active agent;
ii. at least one acid free or substantially free of carbon-carbon double bonds;
iii. optionally at least one cationic polymer; and
iv. optionally a cosmetically acceptable solvent;

wherein the system or composition comprising the system is substantially free of crosslinking compounds.

It to be understood that, as used herein the terms "the," "a," or "an," mean "at least one," and should not be limited to "only one" unless explicitly indicated to the contrary. Thus, for example, reference to "a portion" includes examples having two or more such portions unless the context clearly indicates otherwise.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

EXAMPLES

The ingredient amounts in the compositions/formulations described below are expressed in % by weight, based on the total weight of the cosmetic composition/formula, unless otherwise indicated.

Example 1

The cosmetic composition of Table 1 was prepared as follows: to glycerin, 4,9-dioxa-1,12-dodecanediamine*, hexadimetherine chloride, and acid (slowly) were added while the solution was mixed. Additional glycerin was added to QS the solution to 100 g. A 1:1:0.267 mix ratio of bleach powder to 30V Oxidizer to additive was prepared (e.g., 30 g bleach powder, 30 g developer, 8 g additive).

TABLE 1

| INCI ingredient | Formula A - % by weight |
|---|---|
| HEXADIMETHRINE CHLORIDE (60%) | 20 |
| GLYCERIN | QS |

TABLE 1-continued

| INCI ingredient | Formula A - % by weight |
|---|---|
| DIAMINE* CAS 7300-34-7 | 5 |
| ACID (Citric) pH adjuster | 16 |

The composition was applied to hair, and the cysteic acid data was evaluated.

Cysteic acid was reduced by about 15% when compared to a bleach standard that has the same lift.

Example 2

The treatment composition of Table 2, containing an active agent of formula (III) (MEA) and an acid (malonic acid), was prepared and may be applied to the hair before or after a chemical treatment composition, such as a color-altering composition, or may be mixed with a chemical treatment composition, such as a color-altering composition, for simultaneous application therewith.

TABLE 2

Exemplary Treatment Composition

| Component | Formula | Treatment Composition |
|---|---|---|
| Monoethanol-amine (active agent of formula (III)) | $H_2N$―OH | (9.19%) Malonic Acid (86.90%) DI Water (3.91%) MEA pH = 3.08 |
| Malonic acid | HO―C(=O)―CH$_2$―C(=O)―OH | |

Example 3: In Vitro Treatment Compositions

The following exemplary treatment compositions, containing an active agent of formula (III) (MEA) and an acid (malonic acid), as set forth in Table 3, were prepared and adjusted to pH 3, unless indicated. In Table 3, the amounts given are % by weight of the treatment compositions, with the balance of each composition being water. The hair treatment selected was a conventional standard bleach including a bleach composition (30 g) and a developer (30-60 g), and was mixed with the treatment compositions (8 g). The mixture was applied to replicate hair samples, under the recited conditions. The hair samples were then washed and evaluated. All examples were performed to achieve the same level of lift (lightening level). The time was adjusted accordingly. This allows a direct comparison of the level of damage caused to the hair.

Results
Cysteic Acid Data

A portion of hair samples (swatches) of hair were cut and weighed to approximately 20 mg, hydrolyzed under strong acidic conditions for 16 hours at 110° C. Once hydrolyzed, samples were pH adjusted to approximately 1.7 with a solution of lithium hydroxide and analyzed on a Hitachi amino acid analyzer, Model 8900. Amino acid standards obtained from Sigma Aldrich (Ref AAS18) were utilized to calibrate the instrument and to calculate the concentration of amino acids for each of the treatment conditions. Table 3 below shows cysteic acid measurements of the compositions of Table 3, which were compared to samples treated with only a standard bleach (bleach and developer composition) and to compositions not containing the active agent (MEA) and at least one acid (malonic acid).

Since the amount of cysteic acid is an indication of the level of damaged hair, a lower measured concentration indicates that a particular treatment composition provided a protection benefit to the hair fiber. Therefore, the measured concentration of cysteic acid is a marker with respect to the assessment of fiber integrity. An improvement of 10% (% relative change) is typically considered to be statistically significant, demonstrating an increase in the fiber integrity.

TABLE 3

Cysteic Acid Data

| Exemplary Treatment Composition | % Active Agent | moles Active Agent/ 100 g | % Acid | moles Acid/ 100 g | pH | Conditions | Cysteic Acid (g AA/ 100 g AA) |
|---|---|---|---|---|---|---|---|
| Standard Bleach | | | | | | 30 V 50 min | 6.4 |
| MEA + Malonic Acid | 5.52% | 0.090 | 12.80% | 0.123 | 3.01 | 30 V 65 min | 4.7 |
| Standard Bleach | | | | | | 30 V 50 min | 6.5 |
| MEA (decreased conc.) + Malonic Acid | 3.01% | 0.049 | 6.92% | 0.067 | 3.02 | 30 V 60 min | 3.6 |
| Standard Bleach | | | | | | 30 V 50 min | 4.9 |
| MEA (increased conc.) + Malonic Acid | 8.02% | 0.131 | 17.77% | 0.171 | 3.02 | 30 V 80 min | 3.7 |
| Standard Bleach | | | | | | 30 V 50 min | 6.4 |
| MEA + Malonic Acid (increased to pH 6) | 8.00% | 0.131 | 7.00% | 0.067 | 6.10 | 30 V 65 min | 6.1 |
| Standard Bleach | | | | | | 30 V 50 min | 6.7 |
| MEA + Malonic Acid (decreased pH to 2) | 3.00% | 0.049 | 18.00% | 0.173 | 2.11 | 30 V 90 min | 5.2 |

Miniature Tensile Tester Data

Hair samples bleached with standard bleach compositions containing treatment compositions containing MEA were assessed for wet tensile strength using a fiber tensile testing instrument from Dia-Stron known as an MTT (Miniature Tensile Tester). For each sample, 50 fibers were run. From the test, Young's Modulus (elasticity, MPa) and Break Stress (force per unit area required to break the fiber, MPa) were determined. Results of the testing are shown below in Table 4.

TABLE 4

MTT Data

| Composition added to Standard Bleach | wt % Active Agent | moles Active Agent/ 100 g | wt % Acid | moles Acid/ 100 g | pH | Conditions | Elastic Mod. (MPa) | Break Stress (MPA) |
|---|---|---|---|---|---|---|---|---|
| None: Standard Bleach | | | | | | 30 V 50 min | 730.29 | 105.17 |
| MEA + water | 5.49 | 0.090 | — | — | 11.81 | 30 V 45 min | 688.18 | 102.68 |
| MEA (decreased conc.) + Malonic Acid | 3.01 | 0.049 | 6.92 | 0.067 | 3.02 | 30 V 60 min | 878 | 120.46 |
| MEA (increased conc.) + Malonic Acid | 8.02 | 0.131 | 17.77 | 0.171 | 3.02 | 30 V 80 min | 840.21 | 121.73 |
| MEA + Malonic Acid (increased pH to 6) | 8.00 | 0.131 | 7.00 | 0.067 | 6.10 | 30 V 65 min | 688.48 | 101.08 |
| MEA + Malonic Acid (decreased pH to 2) | 3.00 | 0.049 | 18.00 | 0.173 | 2.11 | 30 V 90 min | 688.49 | 104.82 |

Based on the MTT results in Table 4, it is evident that a mixture of bleach with the combination of active agent (MEA) and acid (malonic acid) provides a large improvement in elastic modulus and break stress compared to bleach alone, as well as to active agent alone, for an equivalent lift (lightening level). The combination of active agent and acid demonstrated improved resistance to breakage of hair treated with a mixture comprising the combination.

Strength and Tactile Substance

Hair samples treated with exemplary treatment compositions were tested for tactile substance relative to hair samples treated with active agent (MEA) alone, MEA pH adjusted with hydrochloric acid to pH of about 3, acid (malonic acid) alone, and acid pH adjusted with sodium hydroxide to pH of about 3.

The evaluation for strength (hair that is easy to detangle and comb, having an above average resistance to bend) and tactile substance (smooth surface feel, when pulled maintains elasticity) was carried out visually and by feel by expert evaluators on wet hair sample, and each sample rated for each property. The results are set forth in Table 5 and FIG. 1, where the increase (positive change) and decrease (negative change) are relative to the bleach standard, considered as baseline (0).

TABLE 5A

Sensory-Active Agent (MEA) + Acid (Malonic Acid) (FIG. 1)

| | MEA + Malonic Acid | MEA + nothing | MEA + HCl | MEA + Malonic Acid | Malonic Acid + Nothing | Malonic Acid + NaOH |
|---|---|---|---|---|---|---|
| Strength | −0.5 | 0 | 0.5 | 0.0 | −1.0 | |
| Tactile Substance | 4 | 2 | 2 | −1 | 0 | |

TABLE 5B

Figure 2:
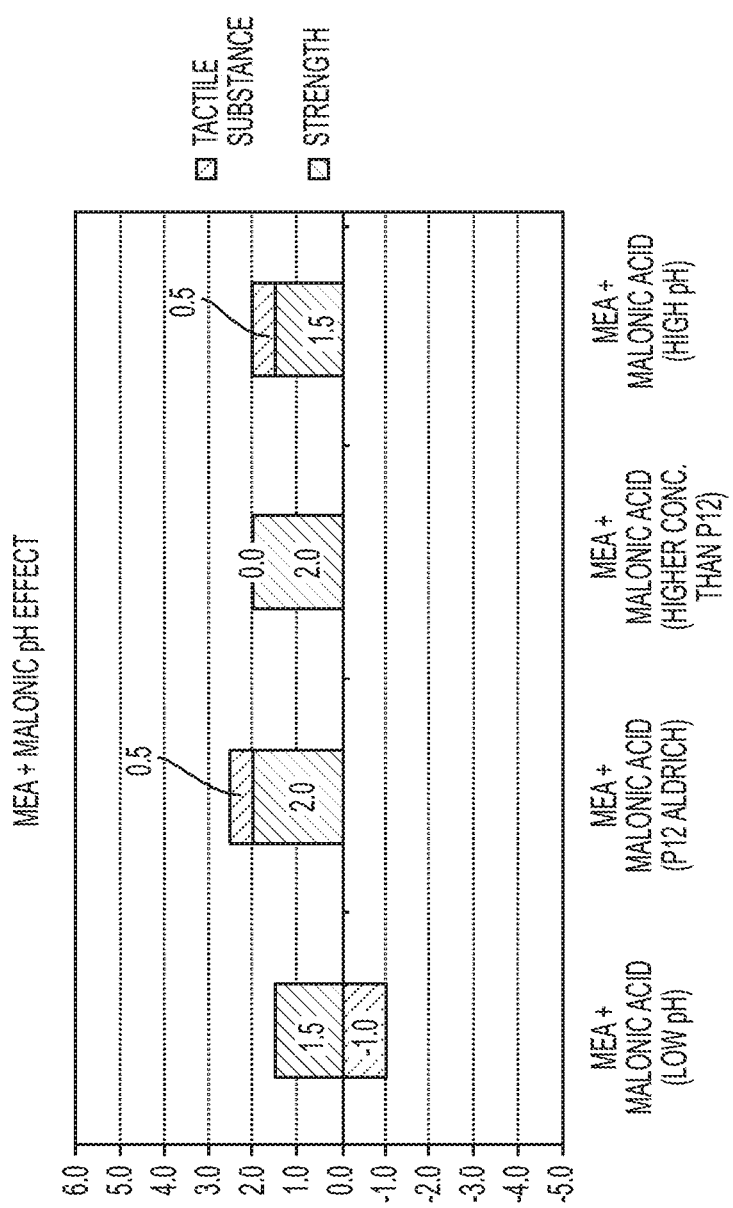
FIG. 2 shows results of pH effect on the sensorial comparison for MEA and malonic acid.

Sensory-Active Agent (MEA) + Acid (Malonic Acid) (pH effect) (FIG. 2)

| | Malonic + MEA pH Effect | MEA + Malonic Acid (Low pH) | MEA + Malonic Acid | MEA + Malonic Acid (higher conc.) | MEA + Malonic Acid (High pH) | MEA + Malonic Acid (higher conc.) |
|---|---|---|---|---|---|---|
| Strength | | 1.5 | 2.0 | 2.2 | 1.5 | 2.0 |
| Tactile Substance | | −1.0 | 0.5 | 0.0 | 0.5 | 0.0 |

As can be seen in Tables 5A-5B and FIGS. 1-2, the best combinations of tactile substance and strength resulted from compositions including the active agent and at least one acid.

Example 4: Highlighted Comparisons—Active Agent (MEA)+Acid (Malonic Acid)

Comparison 4A:

A 1:1:0.267 mix ratio of bleach powder to 30V Oxidizer to additive was prepared (e.g., 30 g bleach powder, 30 g developer, 8 g additive). The additive comprised MEA and malonic acid. 10 g of mixture per 1 g of hair of the mixture was applied to dry hair and rinsed after 45 minutes. A conditioner was applied and rinsed from the hair. The hair was then washed with a shampoo and conditioner. The hair was then blow dried. Cysteic acid was reduced by about 16% when compared to a bleach standard that has the same lift.

Comparison 4B:

A 1:1:0.267 mix ratio of bleach powder to 30V Oxidizer to additive was prepared (e.g., 30 g bleach powder, 30 g developer, 8 g additive). The additive comprised MEA and malonic acid. 10 g of mixture per 1 g of hair of the mixture was applied to dry hair and rinsed after 55 minutes. A conditioner was applied and rinsed from the hair. The hair was then washed with a shampoo and conditioner. The hair was then blow dried.

The fiber integrity of the hair was evaluated using a Dia-stron7 Miniature Tensile Tester (MTT). The results are listed in Table 6, below:

TABLE 6

MTT Data for MEA + Malonic Acid, Comparison 4B

| Composition | Elastic Modulus (MPa) | Break Stress (MPa) |
|---|---|---|
| Bleach alone | 701.3 | 93.1 |
| Mixture with additive | 858.3 | 111.8 |

As shown in Table 6, the elastic modulus and the break stress were higher for the mixture compared to bleach alone.

Comparison 4C:

The identical process of application was repeated three times. The fiber integrity of the hair was evaluated using a Dia-stron7 Miniature Tensile Tester (MIT). The results are listed in Table 7, below:

TABLE 7

MTT Data for MEA + Malonic Acid, Comparison 4C

| Composition | Elastic Modulus (MPa) | Break Stress (MPa) |
|---|---|---|
| Bleach alone | 876.3 | 119.7 |
| Mixture with additive | 1043.8 | 133.2 |

As shown in Table 7, the elastic modulus and the break stress were higher for the mixture compared to bleach alone.

Comparison 4D:

A 1:1:0.267 mix ratio of bleach powder to 40V Oxidizer to additive was prepared (e.g., 15 g bleach powder, 15 g developer, 4 g additive). The additive comprised MEA and malonic acid. 10 g of mixture per 1 g of hair of the mixture was applied to dry hair and rinsed after 10 minutes. A conditioner was applied and rinsed from the hair. The hair was then washed with a shampoo and conditioner. The hair was then blow dried. The process was repeated for a total of three times.

The hair was subjected to 10,000 strokes with a brush. The broken fibers were counted and the results are listed in Table 8, below:

TABLE 8

Analysis of Broken Fibers for MEA + Malonic Acid, Comparison 4D

| Composition | Broken Fibers (average of 8 samples) |
|---|---|
| Bleach alone | 114.13 |
| Mixture with additive | 44.88 |

As shown in Table 8, the number of broken fibers was higher for the bleach alone compared to the mixture.

The results of Comparisons 4A-4D demonstrate that treatment of hair with a combination of active agent with an acid during a bleaching process provides significant reduction in cysteic acid, as well as increase in resistance to breakage, relative to hair treated with the bleaching formulation alone.

What is claimed is:

1. A method for altering the color of the hair, comprising applying to the hair:
    (a) a hair treatment composition comprising:
    monoethanolamine;
    at least one compound chosen from malonic acid and salts thereof; and
    at least one solvent chosen from water, cosmetically acceptable organic solvents, and combinations thereof,
    wherein the monoethanolamine is present in an amount ranging from about 3% to about 8% by weight, based on the weight of the hair treatment composition;
    wherein the at least one compound chosen from malonic acid and salts thereof is present in an amount ranging from about 6% to about 18% by weight, based on the weight of the hair treatment composition; and
    wherein the pH of the hair treatment composition ranges from about 2 to about 6; and
    (b) a color-altering composition comprising at least one oxidizing agent, at least one colorant compound, or combinations thereof;
    wherein the hair treatment composition and the color-altering composition are free of oxidative dye precursors.

2. The method of altering the color of the hair according to claim 1, wherein said hair treatment composition comprises monoethanolamine in an amount of about 3% and the at least one compound chosen from malonic acid and salts thereof in an amount of about 7% by weight, based on the weight of the hair treatment composition.

3. The method of altering the color of the hair according to claim 1, wherein said hair treatment composition comprises monoethanolamine in an amount of about 8% and the at least one compound chosen from malonic acid and salts thereof in an amount of about 18% by weight, based on the weight of the hair treatment composition.

4. The method of altering the color of the hair according to claim 1, wherein said hair treatment composition further comprises at least one colorant compound other than oxidative dye precursors.

5. The method of altering the color of the hair according to claim 1, wherein said hair treatment composition further comprises at least one additional compound chosen from acids and salts thereof.

6. The method of altering the color of the hair according to claim 5, wherein the at least one additional compound chosen from acids and salts thereof is chosen from amino acids, citric acid, hydrochloric acid, phosphoric acid, carbonic acid, acetic acid, glycolic acid, lactic acid, tartaric acid, citric acid, malic acid, glucuronic acid, acidic plant extracts, and the salt of these acids, and mixtures thereof.

7. The method of altering the color of the hair according to claim 1, wherein the at least one oxidizing agent is chosen from peroxides, persulfates, perborates, percarbonates, alkali metal bromates, ferricyanides, peroxygenated salts, and mixtures thereof.

* * * * *